(12) United States Patent
Milton

(10) Patent No.: US 11,534,337 B2
(45) Date of Patent: Dec. 27, 2022

(54) CONTACT LENS TOOL KIT AND METHOD OF USING

(71) Applicant: Invent Horizon, LLC, Raleigh, NC (US)

(72) Inventor: David Timothy Milton, Raleigh, NC (US)

(73) Assignee: Invent Horizon, LLC, Raleigh, NC (US)

( * ) Notice: Subject to any disclaimer, the term of this patent is extended or adjusted under 35 U.S.C. 154(b) by 437 days.

(21) Appl. No.: 16/890,509

(22) Filed: Jun. 2, 2020

(65) Prior Publication Data

US 2020/0297532 A1   Sep. 24, 2020

Related U.S. Application Data

(63) Continuation-in-part of application No. 15/295,956, filed on Oct. 17, 2016, now Pat. No. 10,667,945, which is a continuation-in-part of application No. 14/849,489, filed on Sep. 9, 2015, now Pat. No. 9,498,375.

(60) Provisional application No. 62/242,334, filed on Oct. 16, 2015, provisional application No. 62/048,176, filed on Sep. 9, 2014.

(51) Int. Cl.
*A61F 9/00* (2006.01)

(52) U.S. Cl.
CPC .................................. *A61F 9/0061* (2013.01)

(58) Field of Classification Search
CPC . A61F 9/00; A45C 11/005; B08B 3/04; B08B 1/02

USPC ......................................................... 294/1.2
See application file for complete search history.

(56) References Cited

U.S. PATENT DOCUMENTS

| | | | |
|---|---|---|---|
| 3,344,461 A | 10/1967 | Floor | |
| 5,069,494 A * | 12/1991 | Reinson | A45C 11/005 294/187 |
| 5,538,301 A | 7/1996 | Yavitz et al. | |
| 5,695,049 A * | 12/1997 | Bauman | A45C 11/005 606/107 |
| 5,732,990 A | 3/1998 | Yavitz et al. | |
| 6,866,462 B2 | 3/2005 | Gilliard | |
| 7,410,050 B2 * | 8/2008 | Py | A45C 11/005 134/901 |
| 9,095,195 B2 * | 8/2015 | Mori | A61L 12/086 |
| 11,071,644 B2 * | 7/2021 | Greenwood | B65D 85/00 |
| 2002/0063068 A1 | 5/2002 | Faxe et al. | |
| 2009/0121370 A1* | 5/2009 | Barrows | B29D 11/00038 425/470 |
| 2011/0109107 A1 | 5/2011 | Lin | |

* cited by examiner

*Primary Examiner* — Paul T Chin
(74) *Attorney, Agent, or Firm* — Michael Best & Friedrich LLP

(57) ABSTRACT

A contact lens tool kit for placement of a contact lens on an eye is provided. The tool kit may include a contact lens tool. The contact lens tool may include an outer edge for selectively engaging a contact lens. The tool kit may also include a lens housing for containing a contact lens, the lens housing selectively engageable with the tool. Engagement of the tool and the lens housing permits reception of the contact lens by the contact lens tool and disengagement of the two permits removal of the contact lens by the tool. The lens housing may include a removable seal for draining solution through an aperture of the contact lens tool or lens housing.

20 Claims, 34 Drawing Sheets

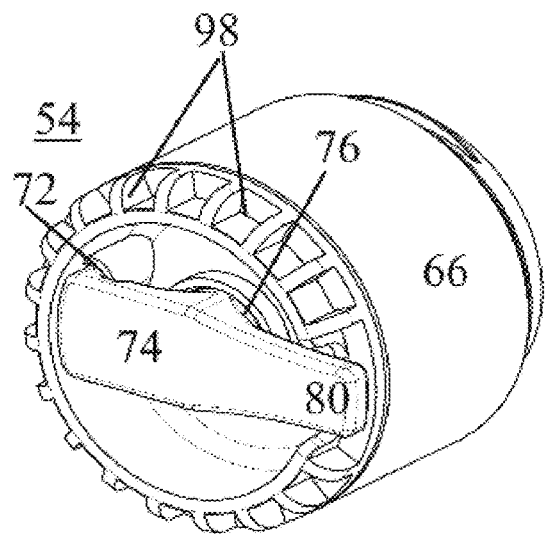
Figure 5A
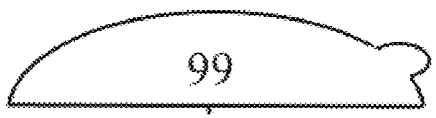
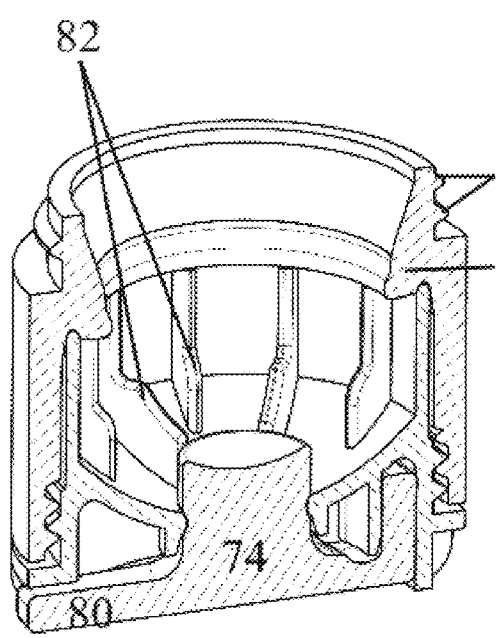
Figure 5B
Figure 5C

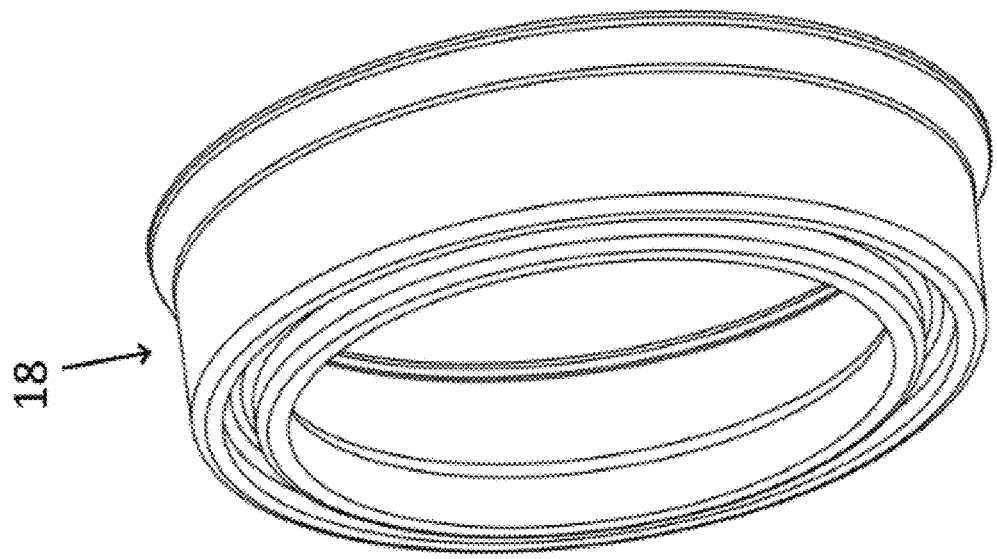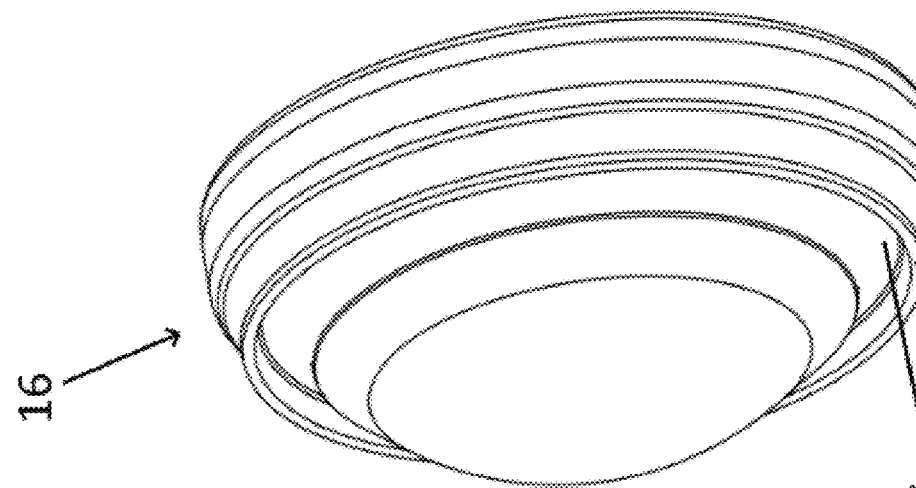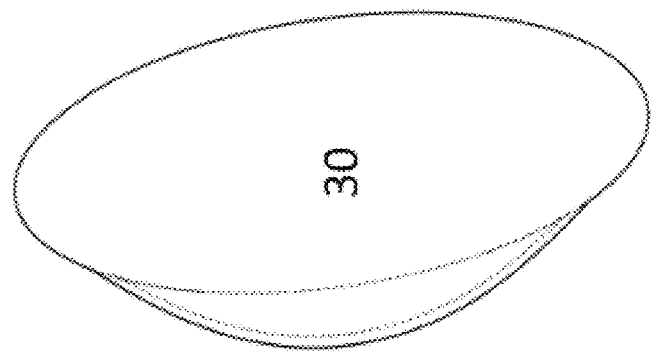
Figure 20

CONTACT LENS TOOL KIT AND METHOD OF USING

CROSS REFERENCE TO RELATED APPLICATIONS

This application is a continuation-in-part of U.S. application Ser. No. 15/295,956 filed Oct. 17, 2016, which is a continuation-in-part of U.S. application Ser. No. 14/849,489 filed Sep. 9, 2015, which claims the benefit of U.S. Provisional Application No. 62/048,176 filed Sep. 9, 2014, each of which are herein incorporated by reference in their entirety. Further, U.S. application Ser. No. 15/295,956 claims the benefit of U.S. Provisional Application No. 62/242,334 filed. Oct. 16, 2015, which is herein incorporated by reference in its entirety.

TECHNICAL FIELD

The present disclosure relates generally to a contact lens tool and tool kit for engaging a contact lens for placement on an eye. More specifically, the present disclosure relates to a contact lens tool having an outer edge and/or annular groove for receiving the contact lens and a tool kit including a lens housing and a tool housing permitting reception of a contact lens by the contact lens tool.

BACKGROUND

Inserting a contact lens can be difficult, for both new users and experienced users alike. Not only is the eye naturally sensitive to touch, but the delicate process of inserting the contact lens properly involves a steep learning curve. It is common for new contact wearers to have several sessions where inserting the contact lens into the eye(s) requires numerous attempts and a significant amount of time, Because of the difficulties associated with inserting contact lenses, many who attempt to use contacts are unsuccessful and may never attempt to wear contacts again.

Another issue common amongst contact lens users is the necessity of making skin-to-lens contact when removing a lens from its storage case and/or when placing the contact lens on the eye. Because fingers may be inserted into the contact lens solution and the contact lens may adhere to the fingers during placement, foreign objects and residue may be introduced into the solution or even directly onto the surface of the contact lens, both of which may result in the objects or residue being introduced to the user's eye, resulting in discomfort or possible infection.

While the technology of the prior art disclose various methods of inserting contact lenses, they fail to teach the ability to easily insert a contact lens into the eye while maintaining sanitary conditions and minimizing the chance that the contact is improperly placed on the eye. Not only is there a risk of introducing foreign matter onto the eye, but inferior placement of the contact lens on the eye could result in air pockets between the contact lens and the eye. Those familiar with wearing contact lenses will appreciate that even minimal errors in the placement of the contact lens on the eye may result in pockets of trapped gas or liquid being formed between the contact lens and the eye during placement.

Notwithstanding the advancements made in the prior art in the field of contact lens storage and use, there remains a need for a contact lens tool kit and tool which improves the ability of a contact lens user to store and use contact lens in a sanitary, easy-to-use manner, while maximizing the chance that each placement of the lens is optimally successful. Additionally, there remains a need for a contact lens tool kit for use with daily wear lenses. Disclosed herein are one or more devices and methods that advantageously address these issues.

SUMMARY

This summary is provided to introduce in a simplified form concepts that are further described in the following detailed descriptions. This summary is not intended to identify key features or essential features of the claimed subject matter, nor is it to be construed as limiting the scope of the claimed subject matter.

According to at least one embodiment, a contact lens tool is provided. The contact lens tool kit includes a first capture portion defining a first outer edge for capturing a first perimeter of a first contact lens; a first stack portion engaged or coupled with the first capture portion, and defining a first stack edge positioned distal the first outer edge and defining a first circumference greater than the first outer edge; an end stack portion defining an end stack edge defining an end circumference greater than the first outer edge and selectively engaged within the first capture portion for creating a fluid-tight seal therebetween.

According to at least another embodiment, the first capture portion and the first stack portion are unitarily formed and are essentially comprised of a deformable material.

According to at least another embodiment, the first capture portion is essentially comprised of a deformable material and is coupled to the first stack portion essentially comprised of a rigid material.

According to at least another embodiment, the first capture portion further defines a first convex lens portion extending between the first outer edge for contouring the first contact lens.

According to at least another embodiment, the first capture portion further defines an annular groove between the first outer edge and the first convex lens portion.

According to at least another embodiment, the contact lens tool further includes a circumferential first wall portion extending away from the first outer edge and towards the first stack portion, the first wall portion defined by the first capture portion or by the first capture portion and the first stack portion.

According to at least another embodiment, the first wall portion defines a first flange externally extending from the first wall portion for creating a seal between the end stack edge and the first capture portion.

According to at least another embodiment, the contact lens tool further includes a floor extending between the first stack edge.

According to at least another embodiment, the floor and/or wall portion defines one or more clefts for permitting fluid flow therethrough.

According to at least another embodiment, the contact lens tool further includes an end floor extending between the end stack edge.

According to at least another embodiment, the end floor defines end ridges for engaging the contact lens and securing the contact lens into position.

According to at least another embodiment, the capture portion defines at least one lens wing extending internally and away from the first contact lens.

According to at least another embodiment, the capture portion defines at least two lens wings and at least one cleft therebetween for permitting fluid flow therethrough.

According to at least another embodiment, the contact lens tool further includes a stack handle extending externally of the stack edge.

According to at least another embodiment, the contact lens tool further includes a stack container for housing the first capture portion, the first stack portion and the end stack portion.

According to at least another embodiment, the stack container defines a plurality of stack arms for selectively engaging the end stack portion.

According to at least another embodiment, the end stack edge defines an aperture therethrough.

According to at least another embodiment, the contact lens tool further includes a seal configured to wrap around the end stack edge and hermitically seal the aperture.

According to at least another embodiment, the contact lens tool further includes a second capture portion defining a second outer edge for capturing a second perimeter of a second contact lens; a second stack portion engaged or coupled with the second capture portion, and defining a second stack edge positioned distal the second outer edge and defining a second circumference greater than the second outer edge; wherein the first stack edge is selectively engaged within the second capture portion for creating a fluid-tight seal therebetween.

According to at least another embodiment, the contact lens tool further includes a stack container for housing the first capture portion, the first stack portion, the end stack portion, the second capture portion and the second stack portion.

BRIEF DESCRIPTION OF THE DRAWINGS

The previous summary and the following detailed descriptions are to be read in view of the drawings, which illustrate particular exemplary embodiments and features as briefly described below. The summary and detailed descriptions, however, are not limited to only those embodiments and features explicitly illustrated.

FIG. 5A is a perspective view of the lens housing according to one or more embodiments of the present invention.

FIG. 5B is a cross-section view of the lens housing according to one or more embodiments of the present invention.

FIG. 5C is a cross-section view of the lens housing and contact lens according to one or more embodiments of the present invention.

FIG. 20 is an exploded view of the capture portion, stack portion and lens according to one or more embodiments of the present invention.

DETAILED DESCRIPTIONS

Figure 1:
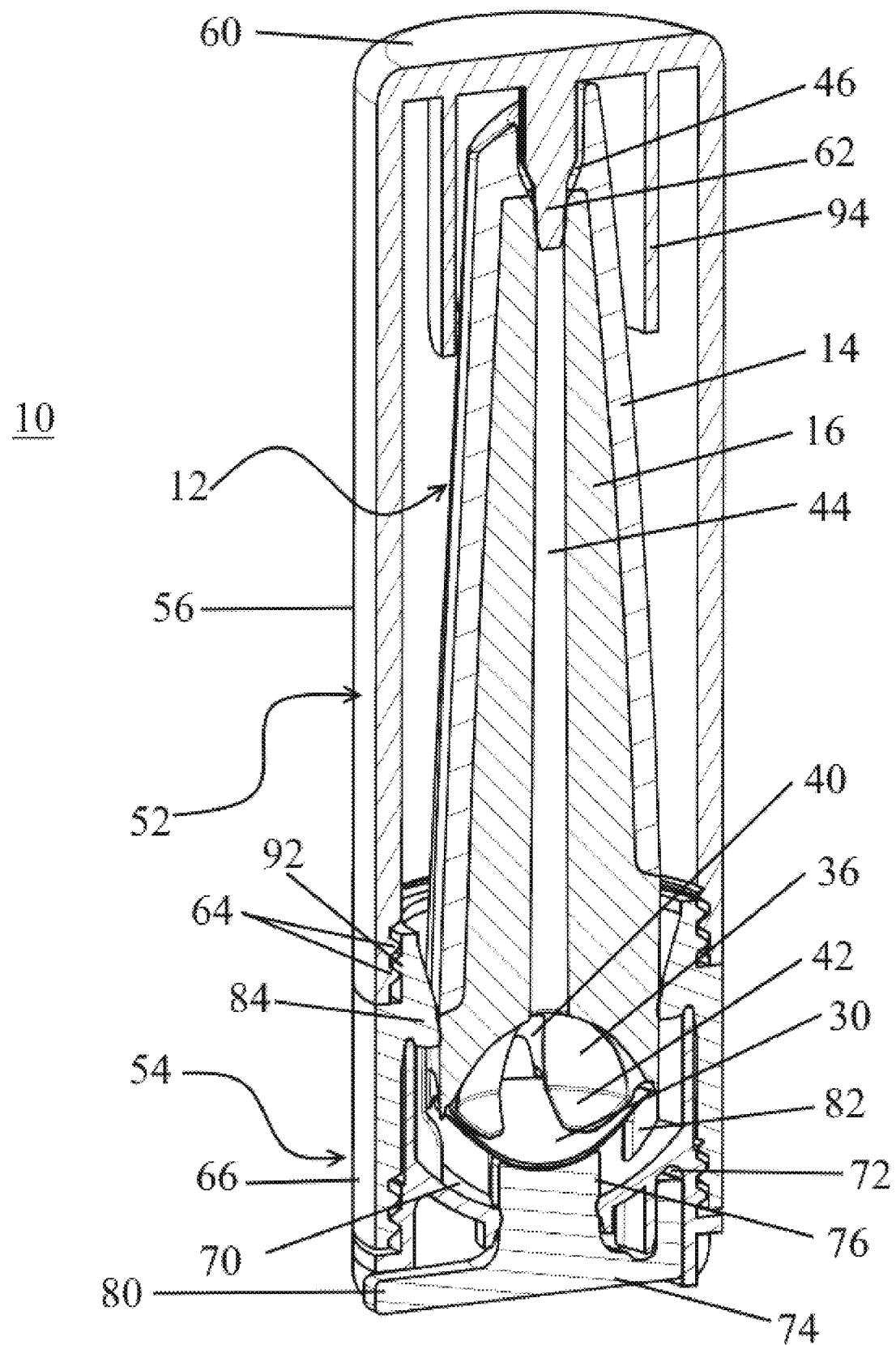
FIG. 1 is a cross-section of the contact lens tool kit according to one or more embodiments of the present invention.

These descriptions are presented with sufficient details to provide an understanding of one or more particular embodiments of broader inventive subject matters. These descriptions expound upon and exemplify particular features of those particular embodiments without limiting the inventive subject matters to the explicitly described embodiments and features. Considerations in view of these descriptions will likely give rise to additional and similar embodiments and features without departing from the scope of the inventive subject matters. Although the term "step" may be expressly used or implied relating to features of processes or methods, no implication is made of any particular order or sequence among such expressed or implied steps unless an order or sequence is explicitly stated.

Any dimensions expressed or implied in the drawings and these descriptions are provided for exemplary purposes. Thus, not all embodiments within the scope of the drawings and these descriptions are made according to such exemplary dimensions. The drawings are not made necessarily to scale. Thus, not all embodiments within the scope of the drawings and these descriptions are made according to the apparent scale of the drawings with regard to relative dimensions in the drawings. However, for each drawing, at least one embodiment is made according to the apparent relative scale of the drawing.

Figure 3:
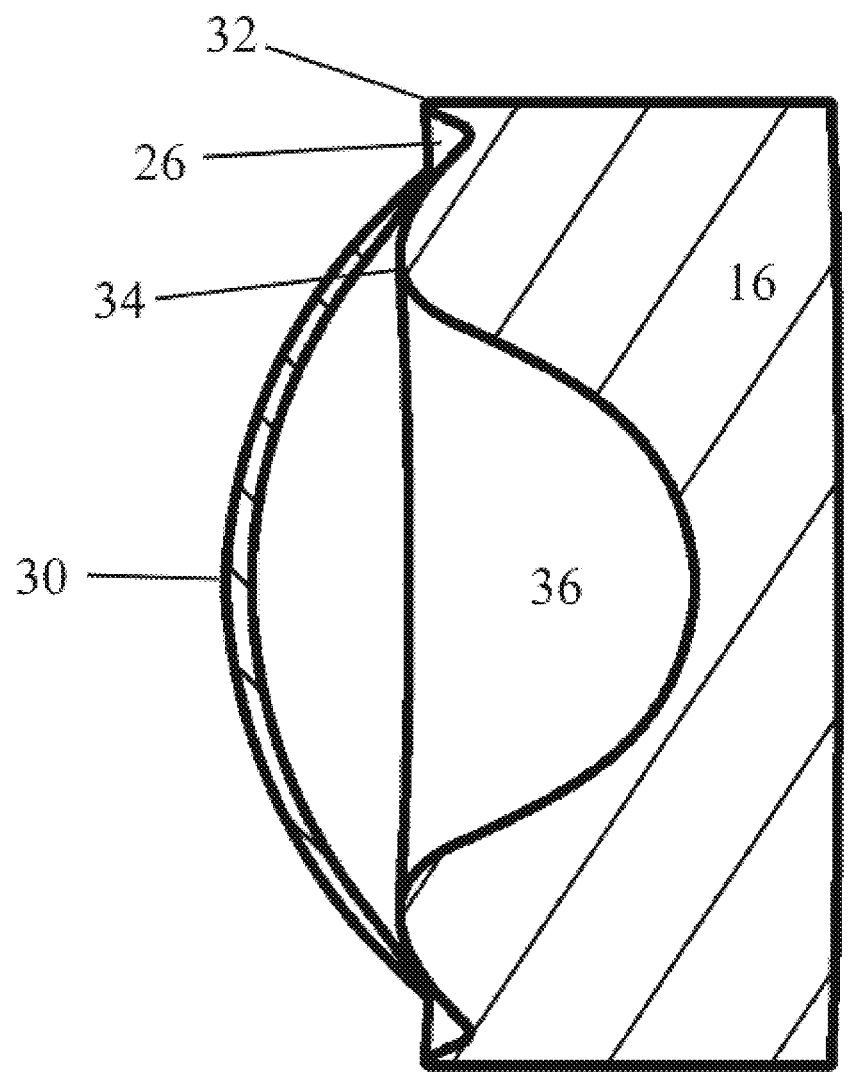
FIG. 3 is cross-section view of the contact lens tool engaged with the contact lens according to one or more embodiments of the present invention.

As will be discussed in more detail herein, this application discloses various embodiments of a contact lens tool kit 10, a contact lens housing 54, a contact lens tool 12, a contact lens tool housing 52 and numerous methods of using these components to aid a contact lens wearer in storing and placing their contact lenses 30. In many embodiments of the present invention, a contact lens 30 is inverted before being placed on the pupil of the wearer's eye, inversion generally meaning that the side of the contact lens 30 that is to directly contact the surface of the eye is convex immediately before being placed, as opposed to being concave when placement is complete. Typically, for a contact lens 30 that has a proper installation direction, the contact lens 30 is concave when the edge of the lens curves inward and convex, or inverted, when the edge flares outward. The methods and components described herein may be applied to either unidirectional or bidirectional contact lenses 30. To reiterate, the inverted contact lens 30 of FIG. 3 is convex, with the surface of the lens 30 to make contact to the eye facing away from the capture portion 16.

By placing a contact lens 30 that is in an inverted form onto the eye, the placement permits the center of the contact lens 30 to make first contact. When the contact lens 30 is being placed on the eye with pressure on the edge of the contact lens 30, contact with the eye causes the contact lens 30 to deform and invert back to its original form, concave. During placement, the contact lens 30 naturally makes additional contact with the eye in a wave-like manner rolling radially outward generally from the center of the contact lens 30. Placing the contact lens 30 on the eye in an inverted manner advantageously permits the contact lens' natural placement motion to push gas and liquid from the center of the contact lens 30 out so that no significant pockets of trapped fluids are formed between the contact lens 30 and the eye during the placement. Once the contact lens 30 fully re-inverts to a concave form, the contact lens 30 is then fully placed onto the eye. As will be described herein, according to some embodiments of the present invention, the pressure on the edge of the contact lens 30 may be provided by the capture portion 16 of the contact lens tool 12.

In alternative embodiments of the methods described herein, the contact lens 30 may initially contact the eye using a portion of the contact lens 30 near the edge of the contact lens, such that the way-Like motion propagates across the contact, still ensuring that the pockets of trapped fluids, gas or liquid, are minimized.

FIG. 1 depicts a contact lens tool kit 10 according to at least one embodiment of this invention. The contact lens tool kit may include a tool housing 52 for housing and/or engaging a contact lens tool 12 and a lens housing 54 for receiving a contact lens 30. The tool housing 52 and lens housing 54 may be selectively engageable with each other. When the tool housing 52 houses the contact lens tool 12 and the lens housing 54 houses a contact lens 30, engagement of the tool housing 52 and the lens housing 54 permits reception of the contact lens 30 by the contact lens tool 12. For example, in one embodiment of this invention, a result of the reception of the contact lens 30 is depicted in FIG. 3, which depicts the capture portion 16 of the contact lens tool 12 engaging the edge of the contact lens 30 using an outer edge and/or annular groove 26. Once the contact lens 30 is received by the contact lens tool 12, insertion of the contact lens 30 into an eye is possible, as described herein.

FIGS. 7-9 and 11 depict a contact lens tool kit 10 according to at least another embodiment of this invention. A tool housing 52 may not be provided in these embodiments. The tool 12 and lens housing 54 may be selectively engageable with each other. The tool 12 and lens housing 54 may be manufactured for single-use. Any component of the kit 10, tool 12 and/or lens housing 54 may be manufactured for disposability. The tool 12 may be engaged with the lens housing 54 such that the contact lens 30 is in engagement with the outer edge 32 and/or annular groove 26 of the capture portion 16 of the tool 12 for insertion. In some embodiments, the capture portion 16 interior of the outer edge 32 may be substantially flat, concave or convex.

Figure 9:
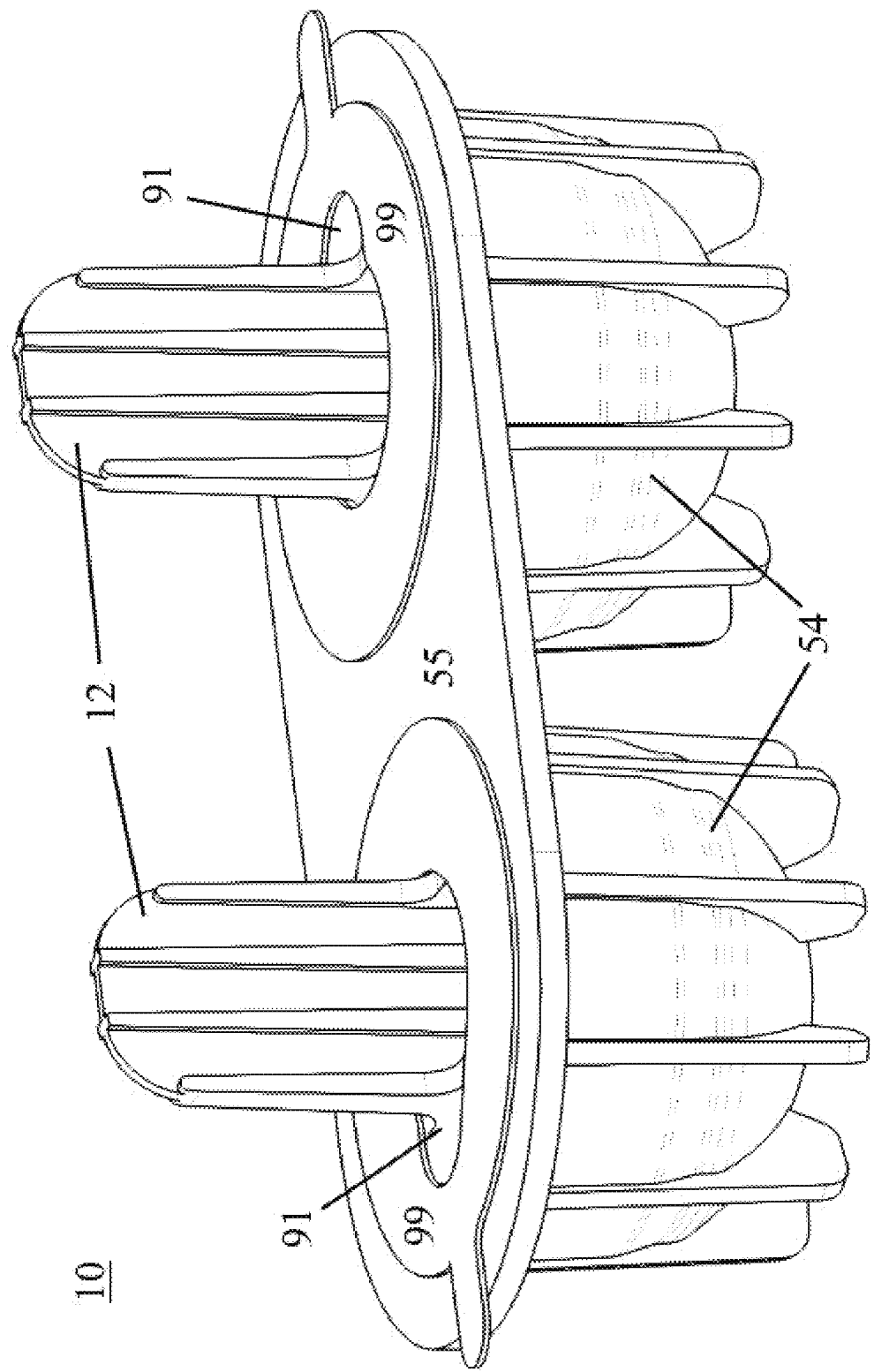
FIG. 9 is a perspective view of a contact lens tool kits have two adjoined lens housings according to one or more embodiments of the present invention.

As is depicted in FIG. 9, two or more lens housings 54 may be adjoined or permanently coupled via a lens housing bridge 55 extending from the lens exterior 56. The lens housing bridge 55 may include a perforation or narrow area for permitting separation of the two lens housing 54. The lens housing exterior 66 may define a plurality of lens housing ridges 67 for permitting the lens housing 54 to rest on a surface. When a plug aperture 76 is defined by the lens housing exterior 66, the drain seal 97 covering the plug aperture 76 may rest substantially co-planar (or substantially parallel and distal from the surface) with the ridges 67 encircling the aperture 76. The ridges 67 may extend from the lens housing exterior 66 and each create a flat bottom portion for contacting the resting surface. Each ridge 67 may extend perpendicularly and circumferentially from the exterior 66.

Figure 33:
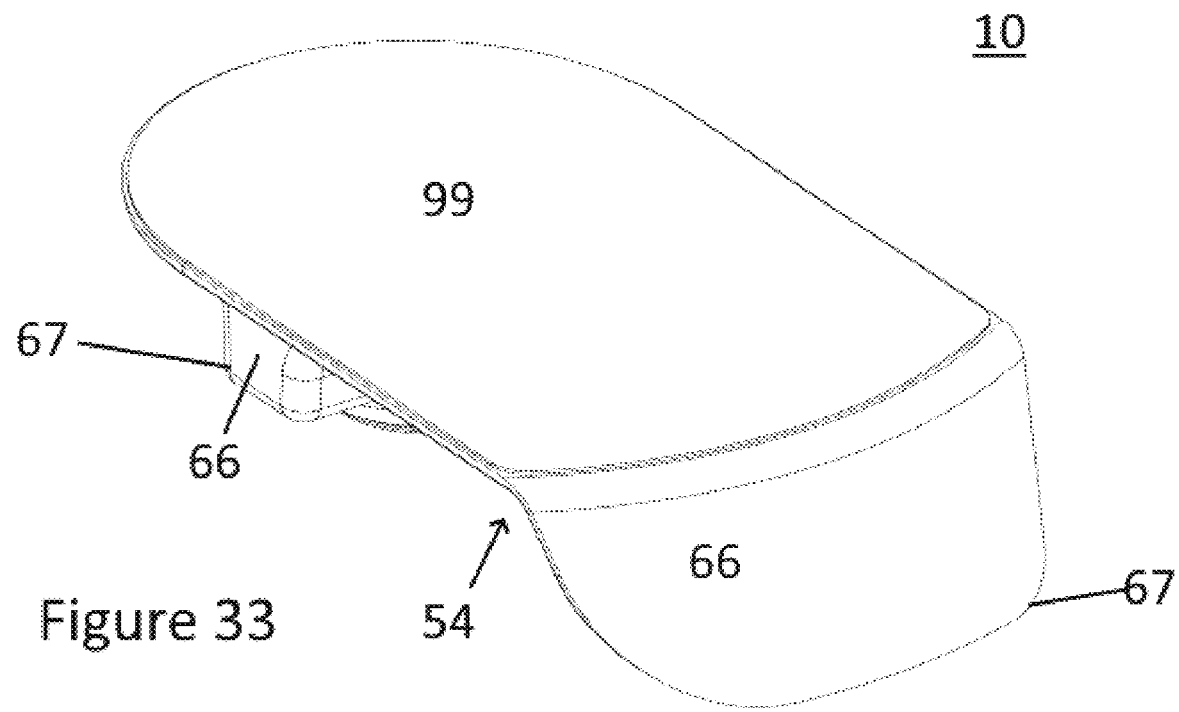
FIGS. 33-36 are perspective views of the contact lens tool including a single-use lens housing according to one or more embodiments of the present invention.

FIGS. 33-36 depict another version of the lens housing 54 according to other embodiments of this invention. FIG. 33 depicts a housing seal 99; which may or may not include a tab 93 for easing removal of the housing seal 99 from the lens housing 54. Further, the lens housing exterior 66 may define a plurality of lens housing ridges 67 for permitting the lens housing 54 to rest on a surface. The ridges 67 may be shaped to conform to the shape of the lens tool 12 housed therein. Similar to other embodiments described herein; the interior 71 of the lens housing may define one or more ribs 82 for contacting the contact lens 30 and creating separation between the lens 30 and the base 70 and/or interior 71 of the lens housing 54.

Figure 34:
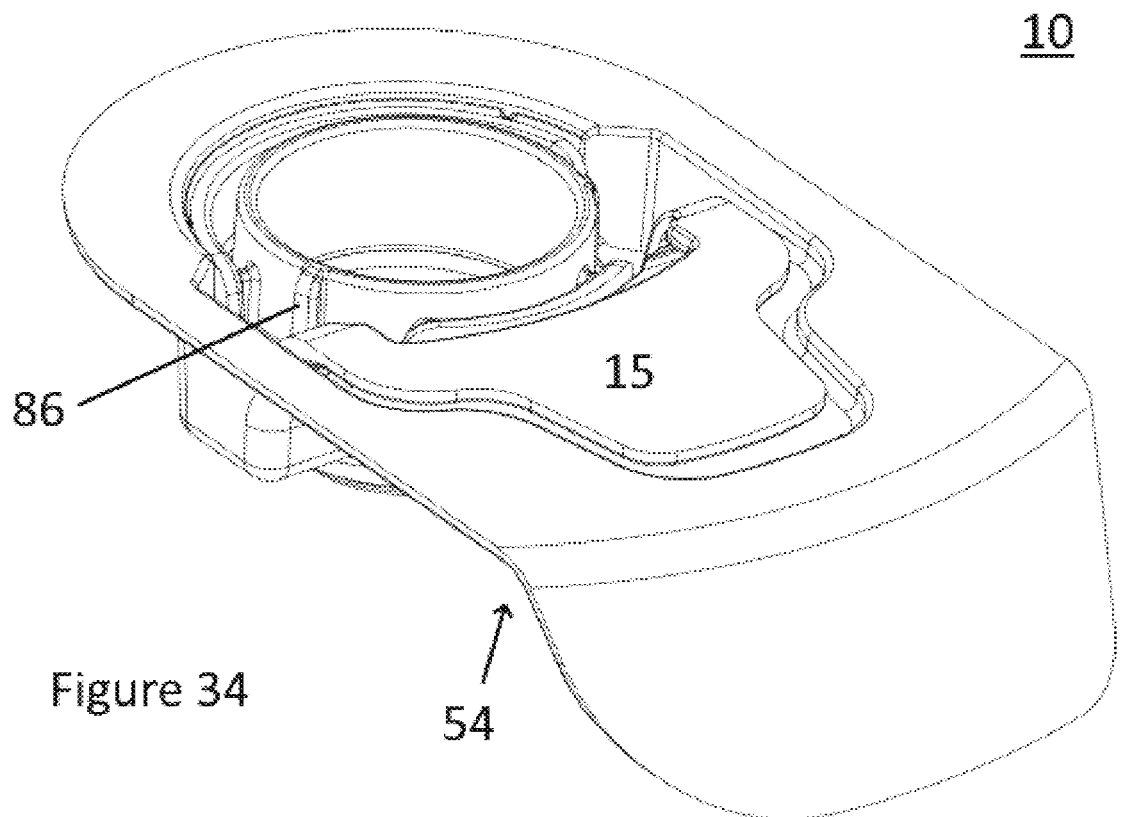
Figure 35:
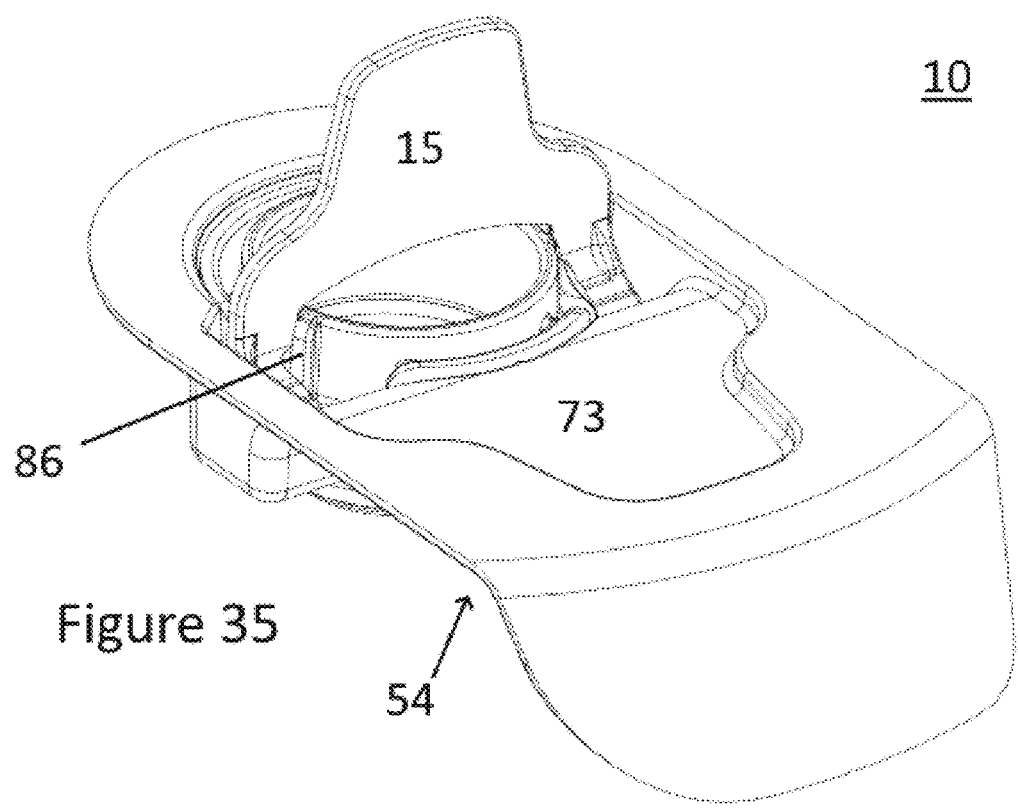
Figure 36:
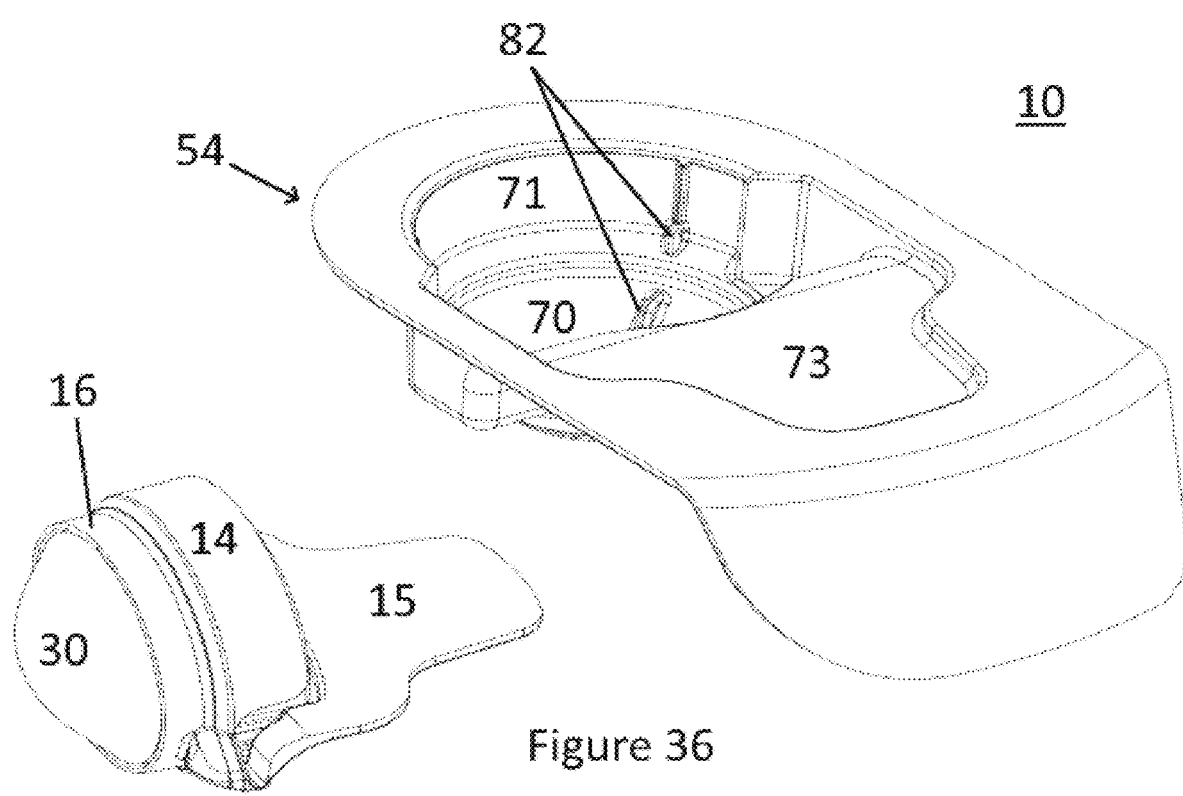

The base 70 and/or interior 71 of the lens housing 54 may define a handle groove 73 for accepting the handle 15 of the lens tool therein when the handle 15 is in the storage position depicted by FIG. 34. The handle 15 may be pivotable between the storage position of FIG. 34 and the use position of FIGS. 35 and 36. As is depicted in FIG. 35, the exterior of the handle portion 14 may define a use ridge 86 for engaging the handle 15 in the use position and providing sufficient friction to prevent the handle 15 from pivoting to the storage position. The handle 15 may be configured to rest in the storage position; but the material of the handle 15, and/or the engagement of the handle 15 with the handle portion 14 may permit pivoting from the storage position to the use position using force. The handle portion 14 of the embodiments depicted in FIGS. 33-36 may be configured similarly to the stack portions 18 depicted in other figures or described herein.

Figure 2A:
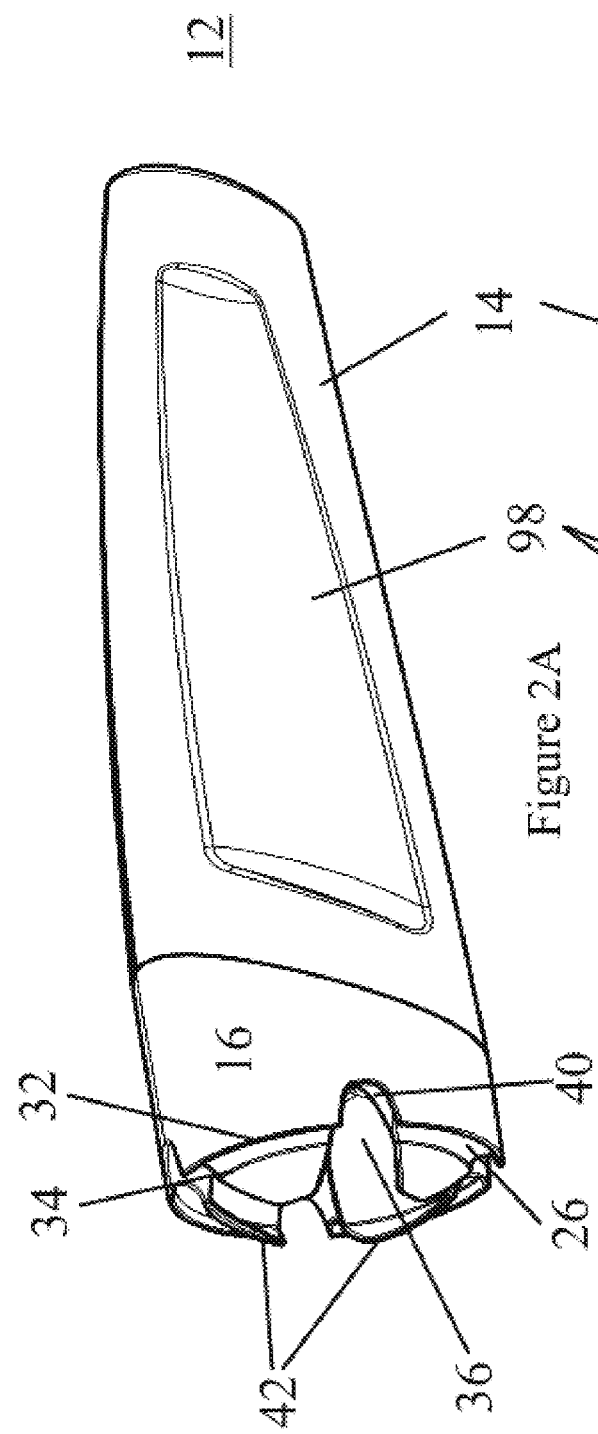
FIG. 2A is a perspective view of the contact lens tool including wings according to one or more embodiments of the present invention.
Figure 2B:
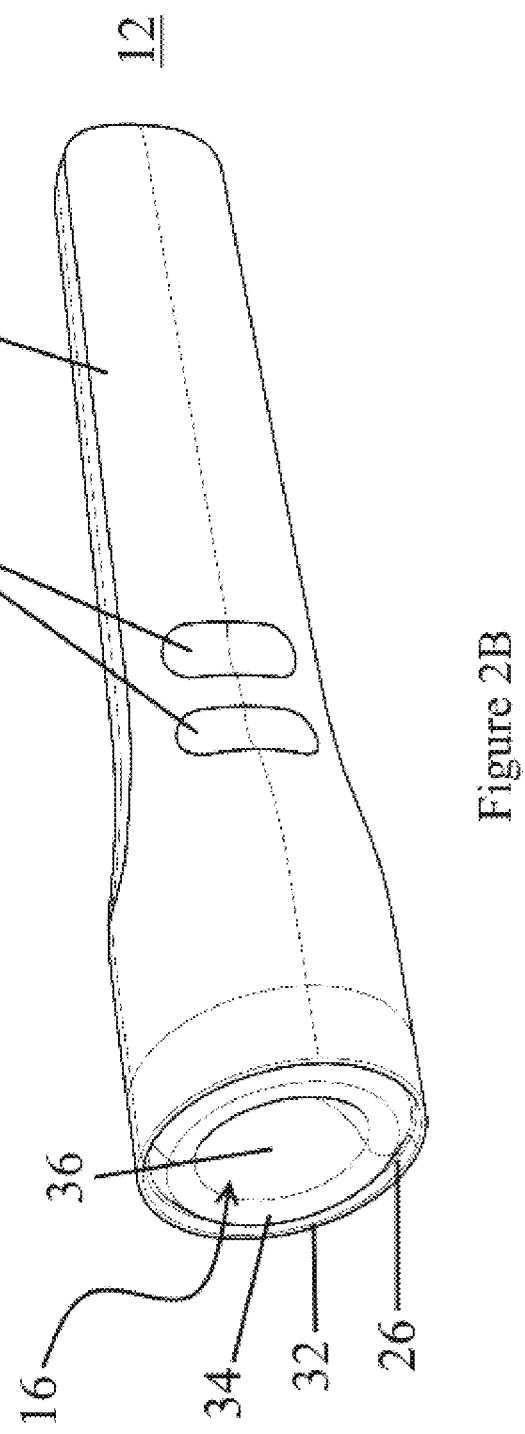
FIG. 2B is a perspective view of the contact lens tool without wings according to one or more embodiments of the present invention.

According to some embodiments, the contact lens tool 12 includes a capture portion 16 for receiving the contact lens 30. FIGS. 2A and 2B depict two embodiments of the capture portion 16, each embodiment depicting the capture portion 16 defining an annular groove 26 and/or an outer edge 32 for releasably engaging the contact lens 30, as depicted in FIG. 2B. The capture portion 16 may also define an interior rise 34 positioned internally of the groove 26 and/or edge 32. Because an annular groove 26 and/or outer edge 32 mirrors the shape of the circular edge of contact lenses 30, engagement of the a contact lens tool 12 having an annular groove 26 and/or outer edge 32 is permitted no matter how the annular groove 26 and/or outer edge 32 is rotated; any position within a 360 degree rotation about the groove 26 and/or edge 32 may result in a successful engagement.

Further, as depicted in the embodiments of FIGS. 2A and 2B, the capture portion 16 may define a hemispherical or spherical cavity 36 positioned internally proximal to the groove 26 and/or the outer edge 32. The cavity 36 may be either concave or convex in shape. For example, FIGS. 2A and 2B depict a concave cavity. A convex cavity 36 may help to create additional engagement with the contact lens 30, thereby supporting the contact lens 30 and preventing the contact lens 30 from displacement during engagement and placement, similar to the wing 42 described herein.

Figure 11:
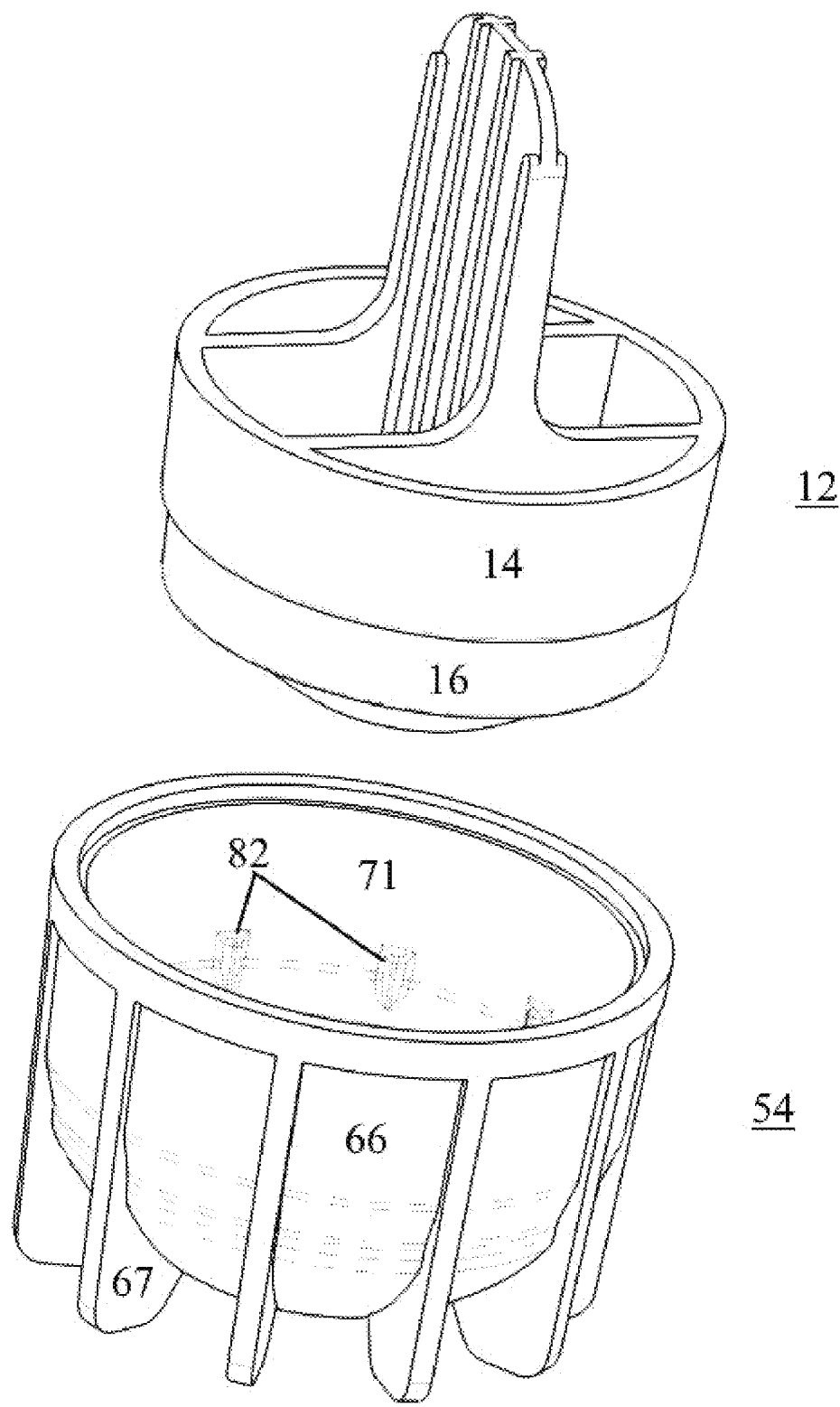
FIG. 11 is a perspective view of the contact lens housing and contact lens tool including a tab handle portion according to one or more embodiments of the present invention.
Figure 12:
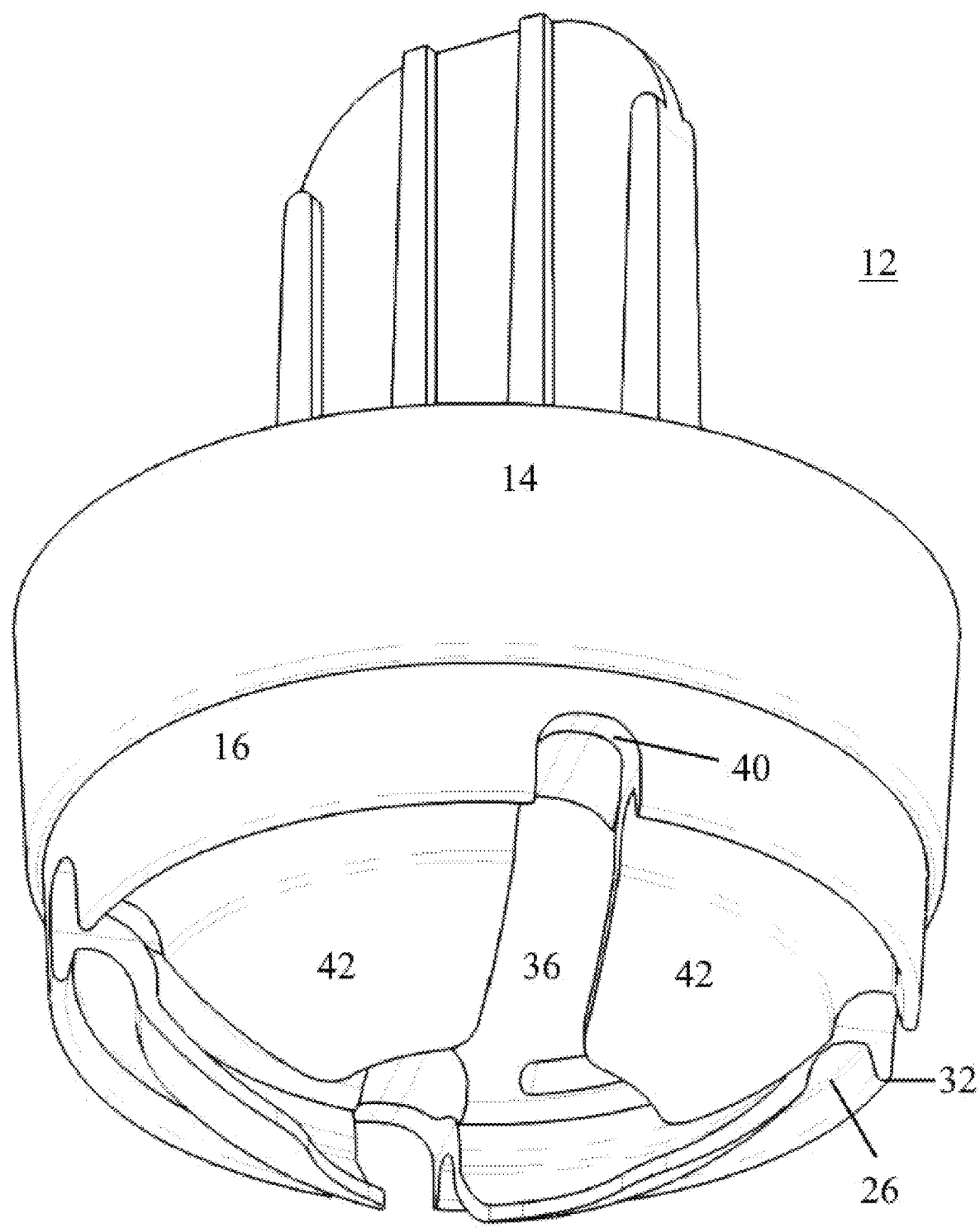
FIG. 12 is a perspective view of the contact lens tool including a tab handle portion according to one or more embodiments of the present invention.
Figure 13:
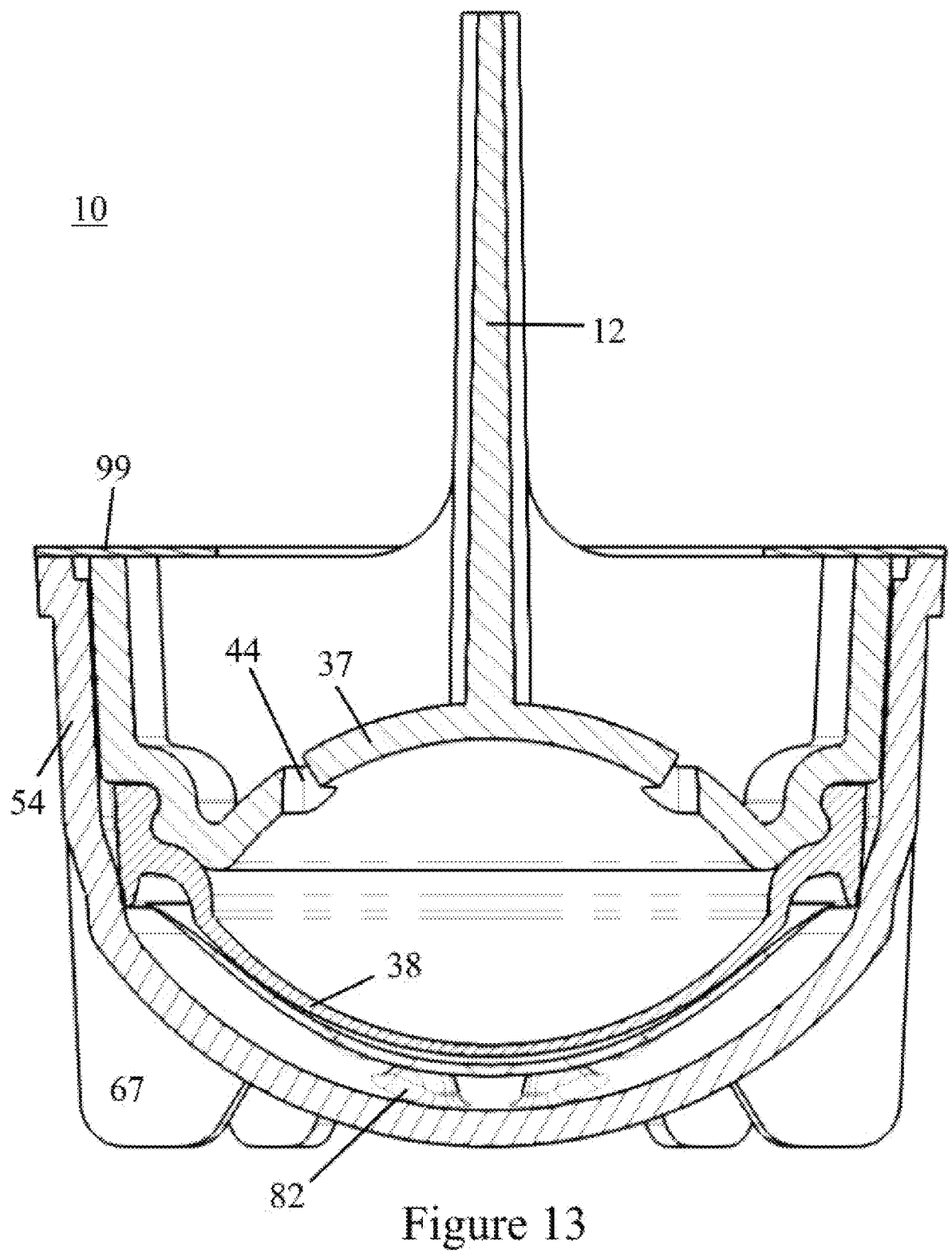
FIG. 13 is a cross-sectional view of the contact lens tool having a spherical cavity and engaged with the lens housing according to one or more embodiments of the present invention.
Figure 14:
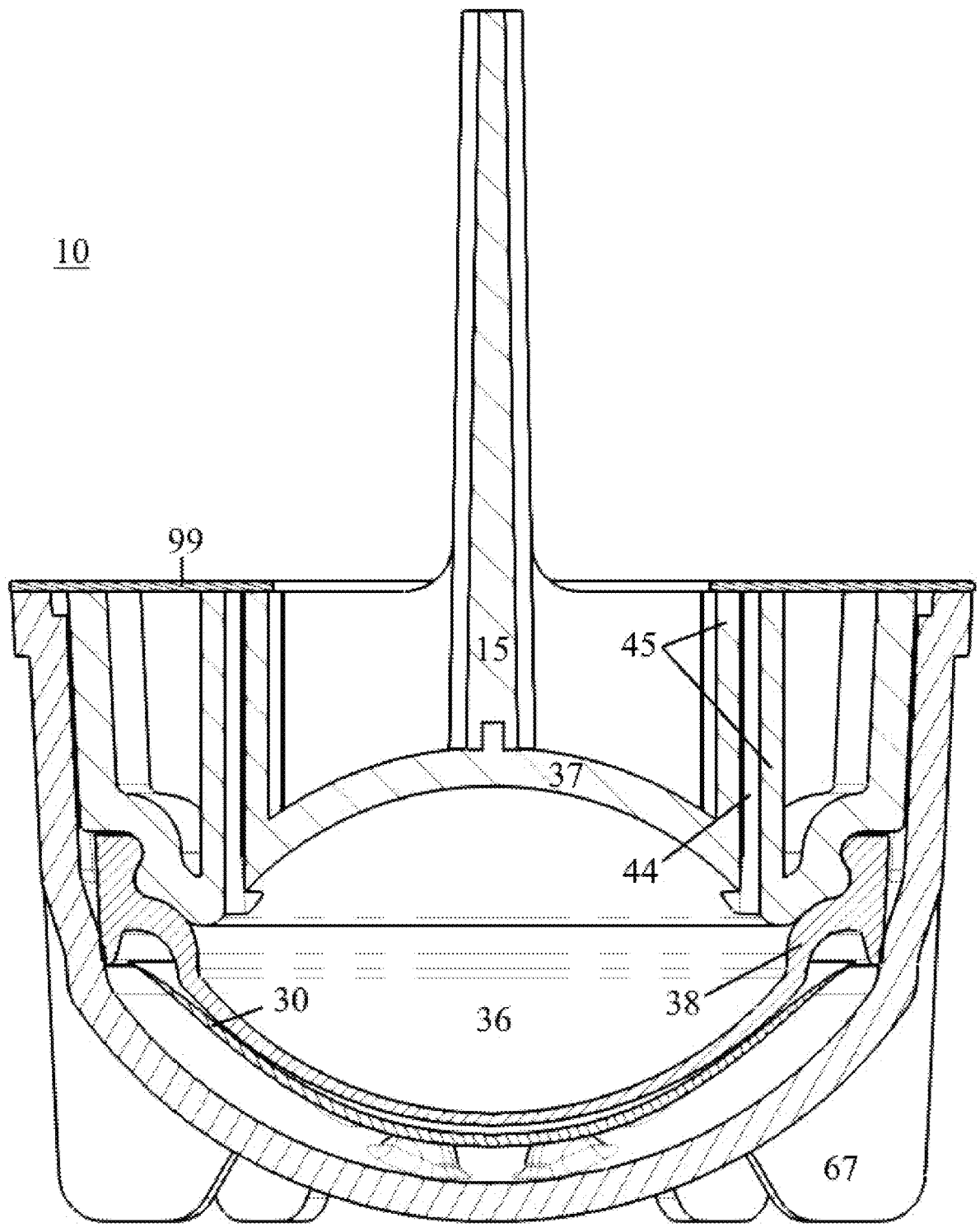
FIG. 14 is a cross-sectional view of the contact lens tool having a spherical cavity and engaged with the lens housing according to one or more embodiments of the present invention.

In FIGS. 11, 13 and 14 a concave, spherical cavity 36 is provided. The cavity 36 may be unitarily constructed or may be constructed using two separate portions. For example, in FIG. 13 a tool portion (or floor) 37 of the cavity 36 is formed by the tool's handle portion 14 and a lens portion 38 of the cavity 36 is formed by the tool's capture portion 16. The tool portion 37 of the handle portion 14 and the lens portion 38 of the capture portion 16 may be selectively engageable via ridges and grooves thereon. The tool portion 37 may be rigid. The lens portion 38 may be deformable. In one embodiment of the method of use, the tool 12 may be removed from the lens housing 54 with the lens 30 engaged to the concave, spherical cavity 36 of the tool 12.

Figure 17:
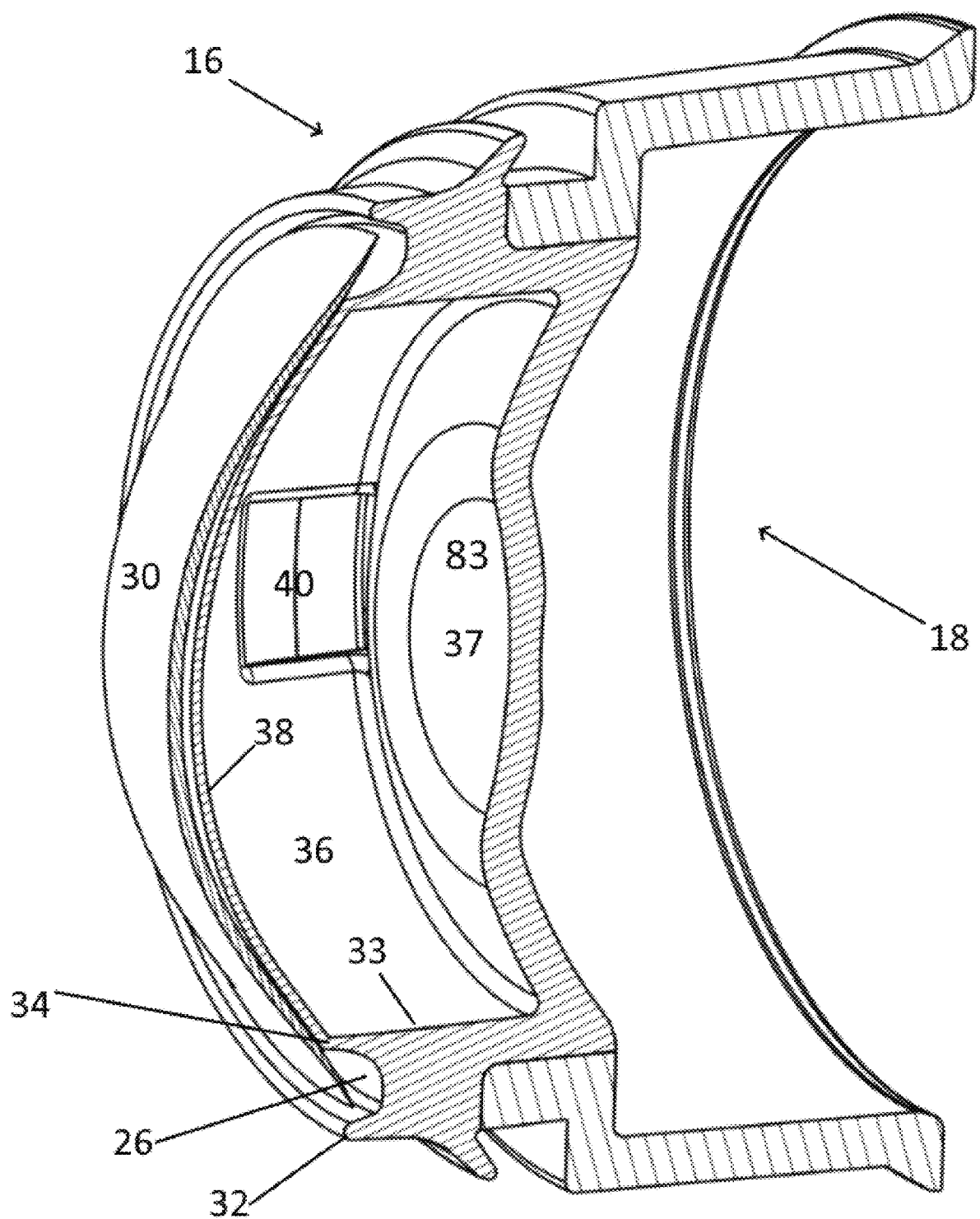
FIG. 17 is a cross-sectional view of the capture portion and the stack portion engaged with a lens according to one or more embodiments of the present invention.
Figure 18:
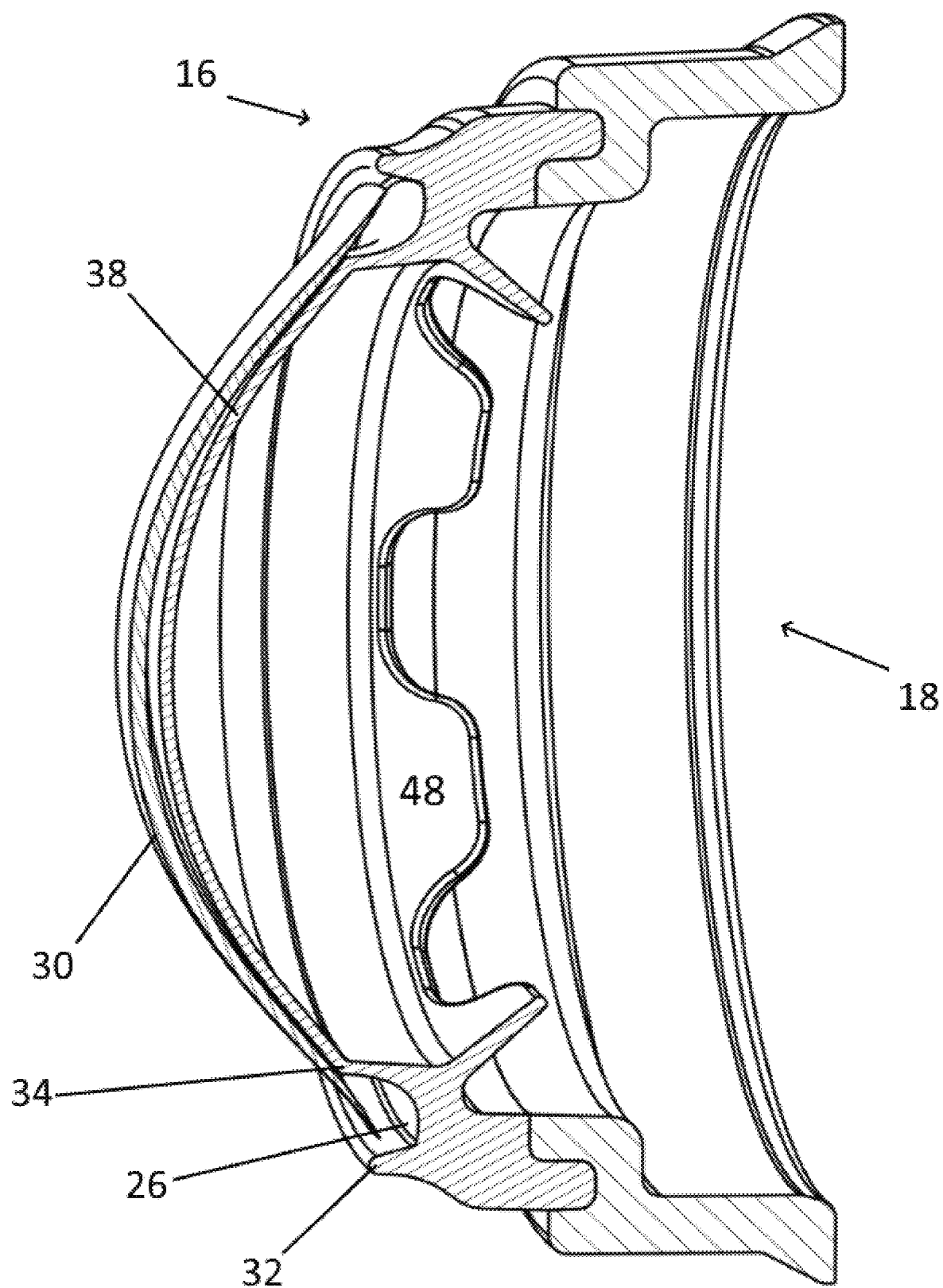
FIG. 18 is a cross-sectional view of the capture portion and the stack portion engaged with a lens and including lens wings according to one or more embodiments of the present invention.
Figure 19:
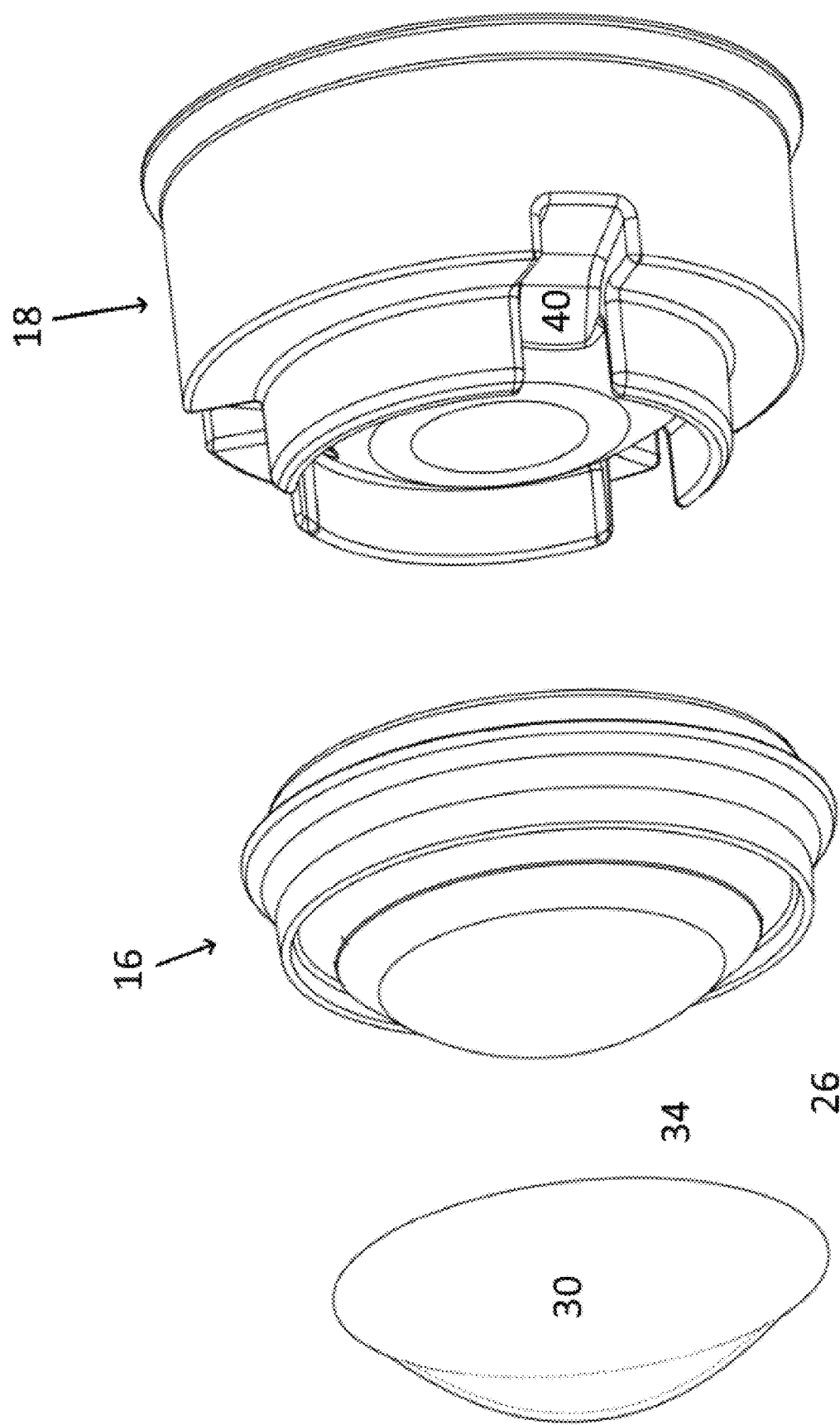
FIG. 19 is an exploded view of the capture portion, stack portion and lens according to one or more embodiments of the present invention.
Figure 23:
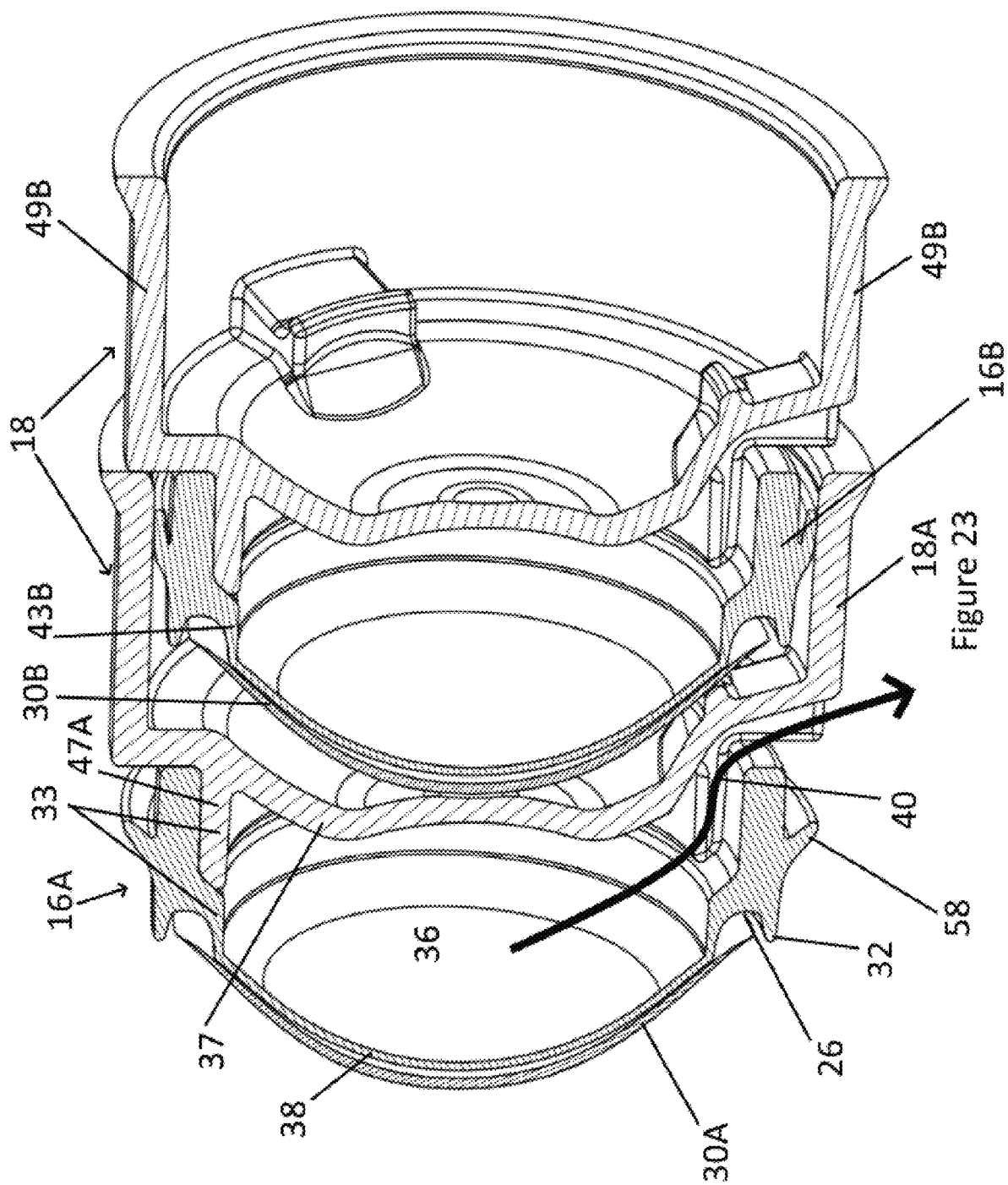
FIGS. 23-26 are cross-sectional views of a stacking configuration of the capture portions and stacking portions according to one or more embodiments of the present invention.
Figure 24:
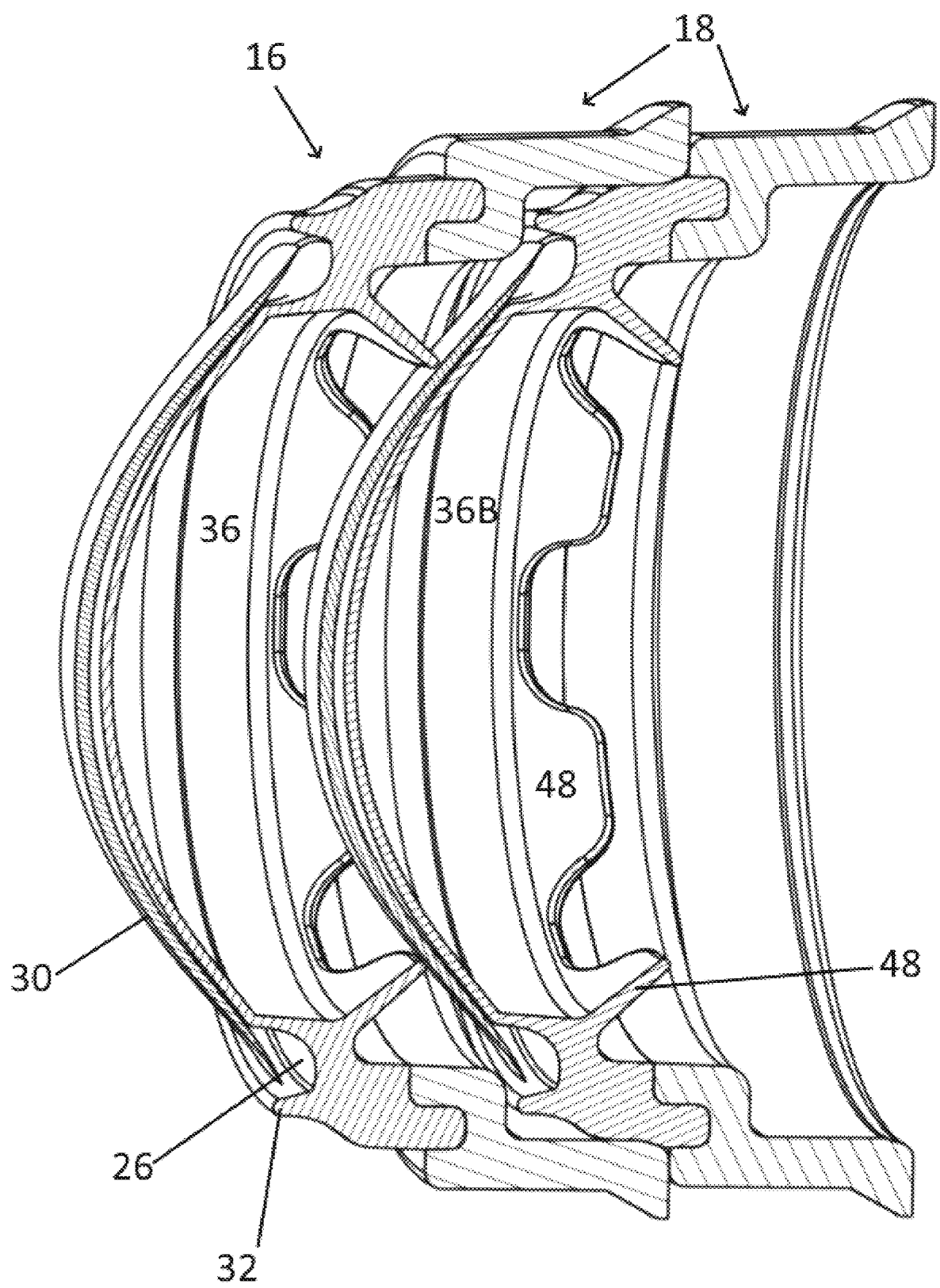
Figure 25:
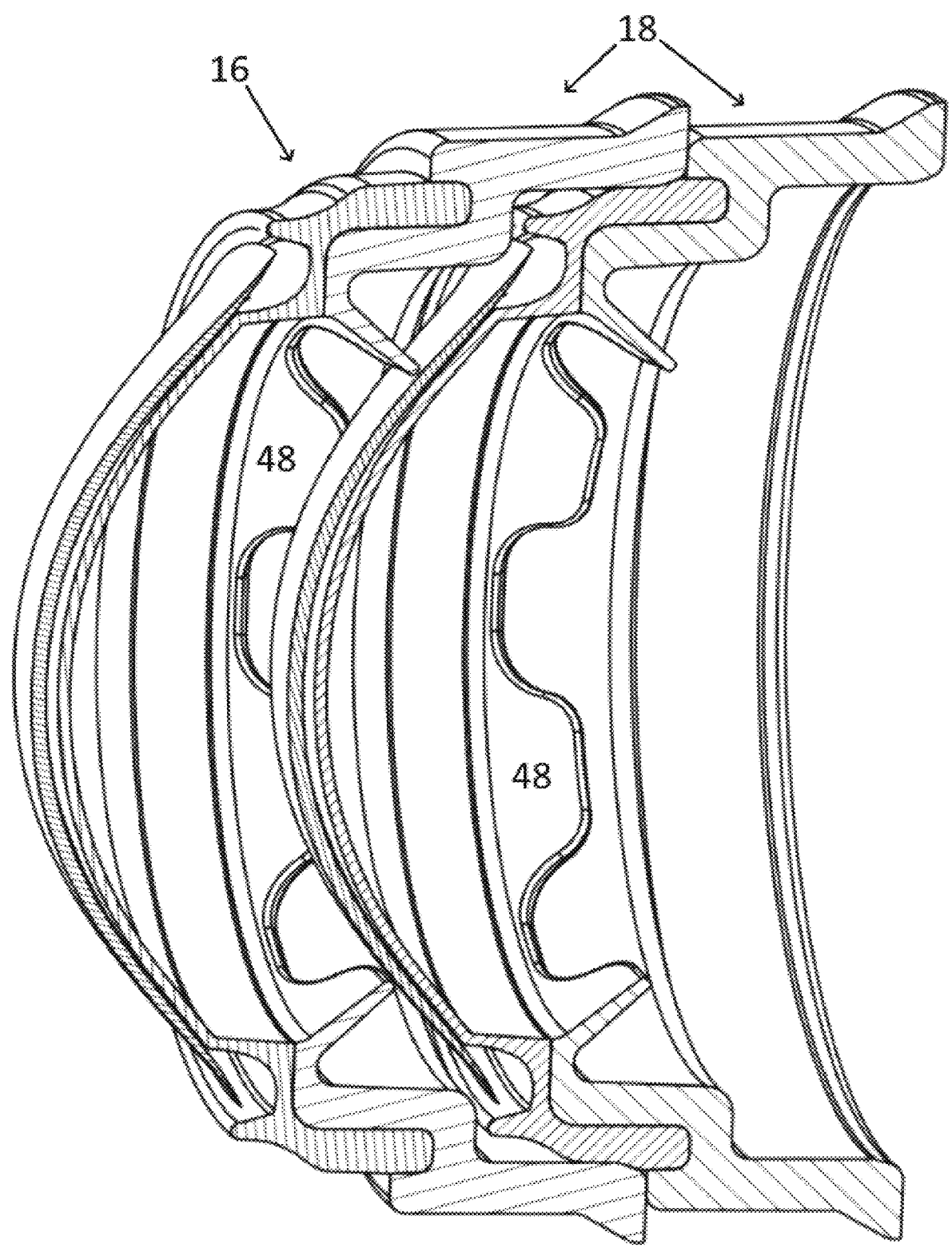
Figure 26:
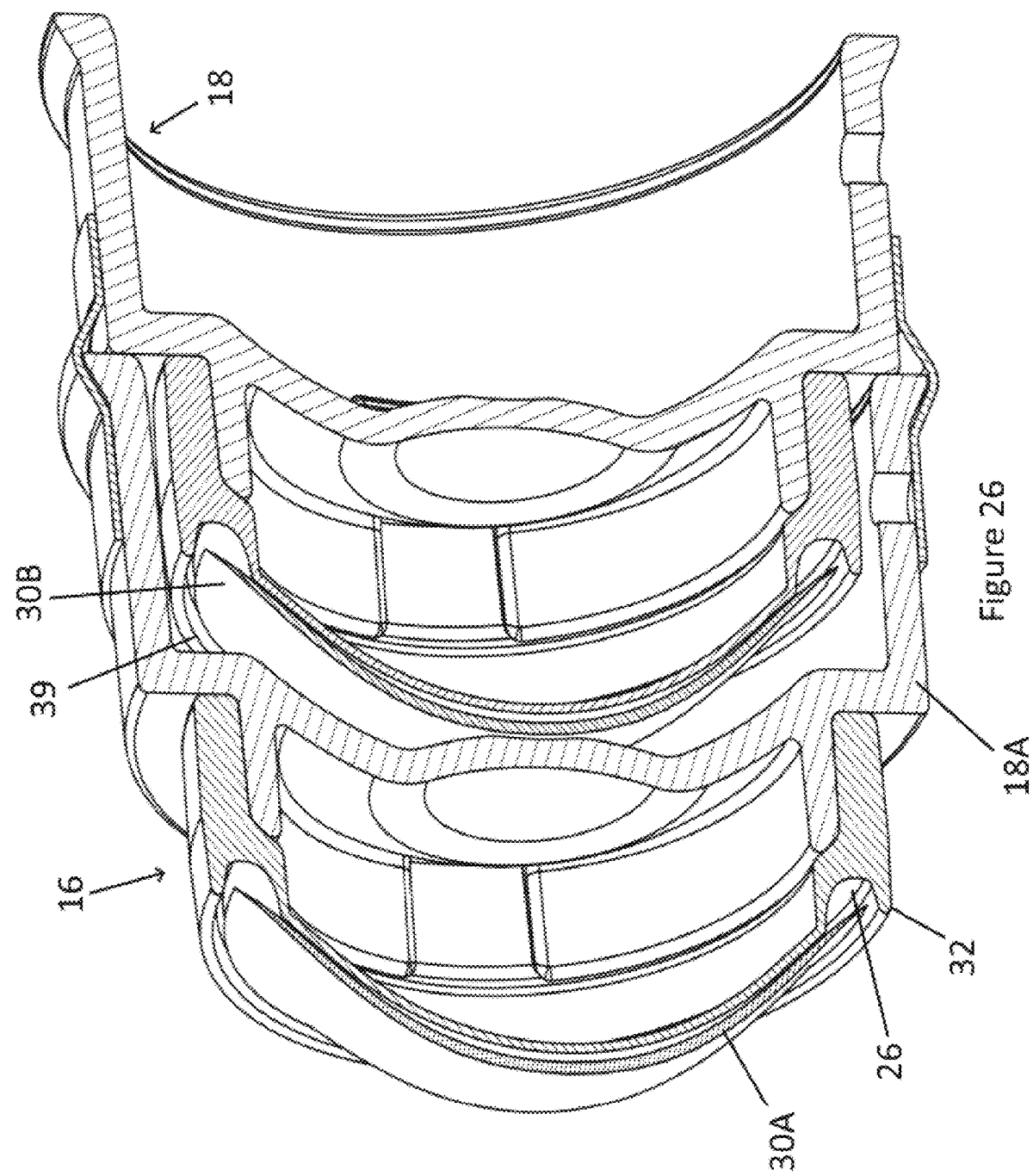

In FIGS. 17-20 and FIGS. 23-26, the lens portion 38 of the cavity 36 is concave and substantially spherical. While the cavity 36 of FIGS. 18, 24 and 25 is not defined by a tool portion 37, the lens portion 38 of the adjacent capture portion 16, and/or the contact lens 30 being captured by the adjacent capture portion 16, serves a similar function as the tool portion 37 of FIGS. 17, 19-20, 23 and 26. Turning specifically to FIG. 17, the cavity 36 is defined by the concave and substantially spherical lens portion 38 opposite the tool portion (or floor) 37, and a wall portion 33 extending between the lens portion 38 and tool portion 37. In FIG. 17 the capture portion 16 includes the tool portion 37 and the wall portion 33. In other embodiments, as depicted in FIGS. 23 and 26, the stack portion 18 includes the tool portion 37, and the wall portion 33 is defined by the capture portion 16 and the stack portion 18.

Figure 15:
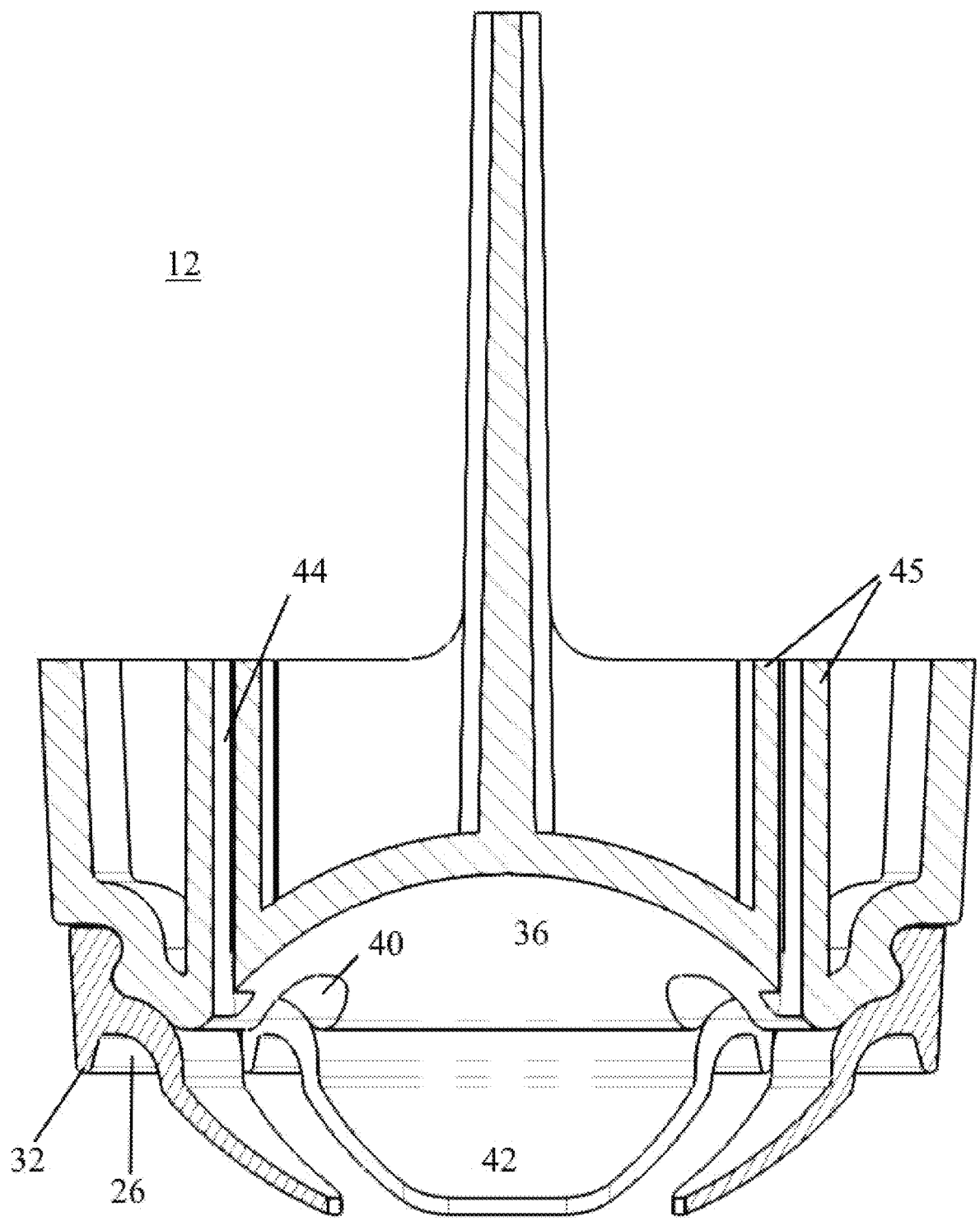
FIG. 15 is a cross-sectional view of the contact lens tool having a hemispherical cavity and engaged with the lens housing according to one or more embodiments of the present invention.
Figure 16:
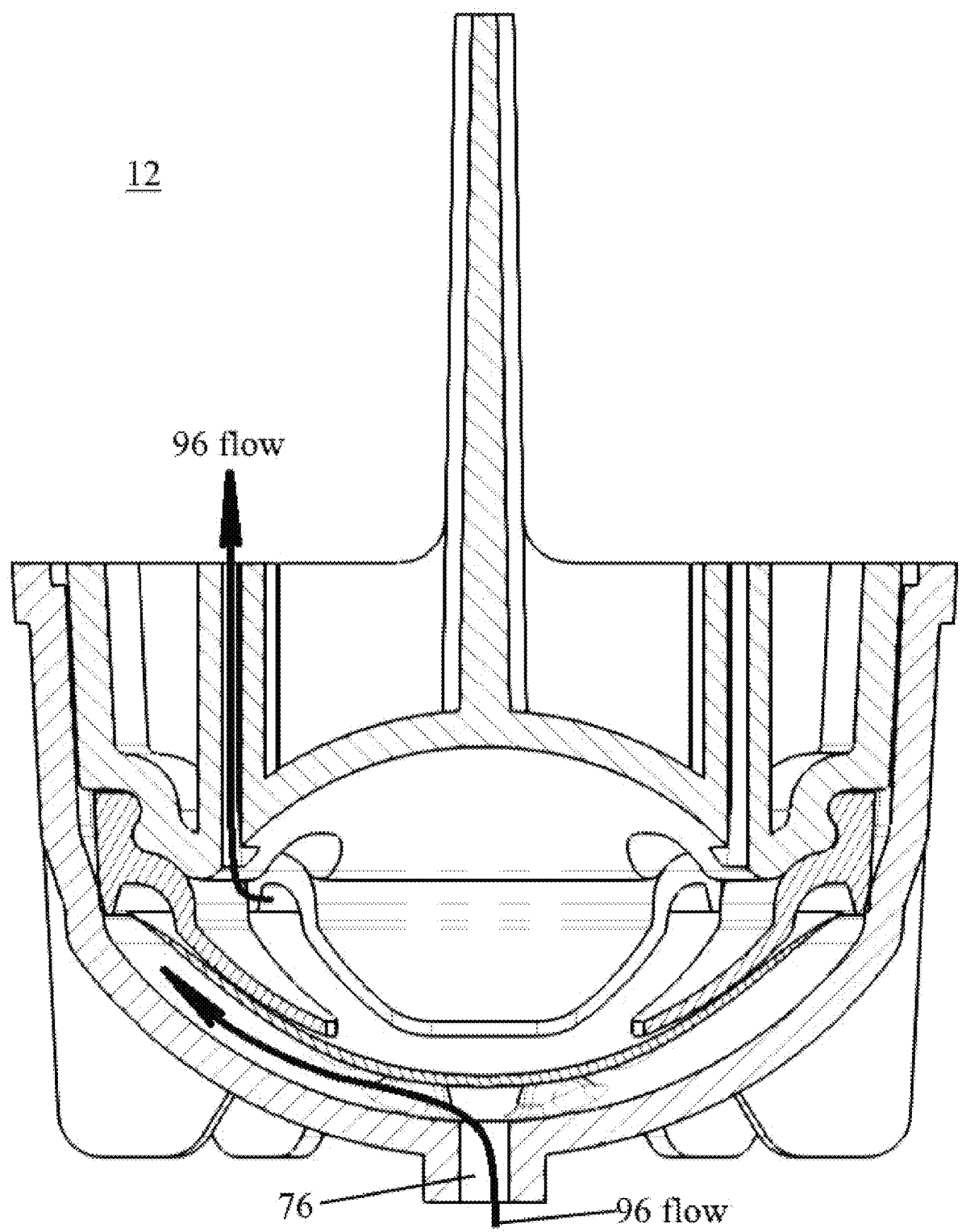
FIG. 16 is a cross-sectional view of the contact lens tool engaged with the lens housing and depicting flowing flow according to one or more embodiments of the present invention.

According to some embodiments, as the lens 30 is placed onto the cornea of the eye, the lens portion 38 of the cavity 36 is deformed inwardly in relation to the cavity 36, thereby pushing fluid through the one or more apertures 44 of the tool portion 37 of the cavity 36. FIG. 14 depicts apertures 44 extending the length of handle protrusions 45 extending from the tool portion 37 of the cavity 36. The housing seal 99 and/or combination seal 95 may cover one end of the apertures 44 proximal from the cavity 36 by extending across the ends of the handle protrusions proximal from the cavity 36 (e.g., FIG. 14). In this manner, there is no free exchange of fluid between the cavity 36 and the surrounding environment when the seal 95, 99 is in place. Alternative embodiments where the capture portions includes wings 42 and clefts 40 are depicted in FIGS. 15 and 16. FIG. 16 also depicts possible fluid flow paths, through the plug aperture 76 and/or through the cleft 40 and aperture 44 of the tool portion 27 of the cavity 36 along the handle 45 protrusions.

In the embodiments depicted in FIGS. 17, 19-20, 23 and 26, the capture portion 16 and/or stack portion 18 may define the cavity 36, which may house fluid. The fluid may be liquid or air. The wall portion 33, and/or the tool portion 37, may define one or more clefts 40 for permitting flow of the fluid housed within the cavity 36 to flow in and out of the cavity 36 as the lens 30 and/or lens portion 38 is deformed. Such fluid flow is depicted in FIG. 23 by the thicker and curved arrow flowing through the cleft 40 from the cavity 36.

In yet other embodiments, as depicted in FIGS. 24 and 25, the cavity 36 may not allow free exchange of fluids between the cavity 36 and the outside environment. In such configurations deformation of the lens 30 and/or lens portion 38 compresses fluid in the cavity 36, and may compress fluid in the adjacent cavity 36B (which may, in turn compress additional adjacent cavities 36).

The interaction and configurations between the stack portion 18 and the capture portion 16 may have numerous embodiments. For example, as depicted in FIG. 17 a flange 58 may extend away from the capture portion 16, opposite the wall portion 33, and towards the stack portion 18. Such an embodiment is similarly depicted in FIG. 23, which illustrates an interaction between a stack edge 49 of the stack portion 18B and the flange 58 of the capture portion 16B for trapping fluid between the capture portion 16B and the adjacent stack portion 18A. In FIGS. 2.3 and 26, the wall portion 33 is comprised of the stack wall 47 and the capture wall 43. In other embodiments, such as FIG. 17, the wall portion 33 is solely comprised of the capture wall. In yet other embodiments, the wall portion 33 may be solely comprised of the stack wall 47.

In FIGS. 23 and 26 a lens cavity 39 is defined for housing fluid for preserving the contact lens 30 therein. Since the volume of fluid positioned between the lens 30 and the lens portion 38 is smaller than the volume of fluid positioned between the lens 30B and the adjacent stack portion 18A, the difference in fluid flows between these two volumes ensures that the lens 30B remains engaged with the capture portion 16B when the adjacent stack portion 18A is disengaged from the capture portion 16B and stack portion 18B. In other words, there is a higher negative pressure between the lens 30B and lens portion 3813 than there is between the lens 30B and stack portion 18A. This fluidic principle also holds true in the embodiments depicted in other figures, such as FIGS. 24 and 25.

In an alternative embodiment, the handle portion 14 may include at least two parts in selective engagement—the handle itself 15 and the tool portion 37. For example, in FIG. 14, the handle 15 may be selectively engageable with the tool portion 37. The selective engagement may be a twist engagement, snap engagement or some other type of engagement. A release button may be provided to disengage the handle 15 from the tool portion 37 so that the handle 15 may be interchanged with another handle 15 or used with another tool portion 37.

The groove 26, edge 32 and/or rise 34 may enable the capture portion 16 of the contact lens tool 12 to engage and hold the contact lens 30 and/or centrally position the contact lens 30 on the lens tool 12, By applying pressure to the edge of the contact lens 30, the contact lens tool 12 enables performance of the methods described herein. In some embodiments, the groove 26, edge 32 and/or rise 34 provides sufficient adherence between the capture portion 16 and the lens 30 to overcome any counter-pressures created within the lens housing 54 (e.g., drainage or travel forces or the adhesive pressure between the lens and the ribs 82, lens base 70, and/or plug 74). Further, the groove 26, edge 32 and/or rise 34 may aid in securing engagement with the contact lens 30 so that the contact lens 30 does not unintentionally become disengaged during use. As will be described herein, the contact lens tool 12 may be used to engage a contact lens 30 housed within a lens housing 54, or, alternatively, the contact lens 30 may be engaged by the contact lens tool 12 independently of a lens housing 54.

Figure 21:
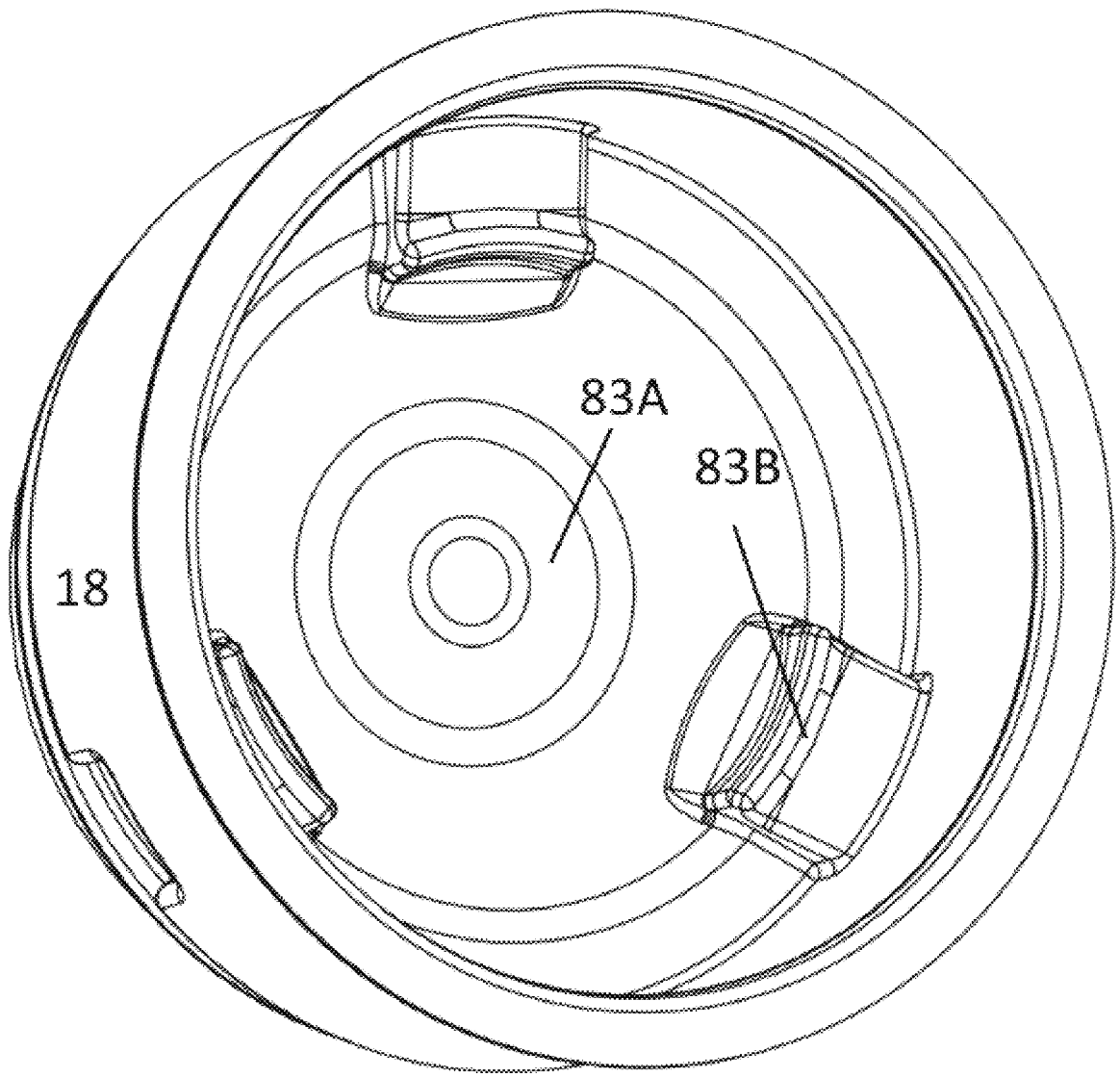
FIG. 21 is an underside view of the stack portion according to one or more embodiments of the present invention.
Figure 22:
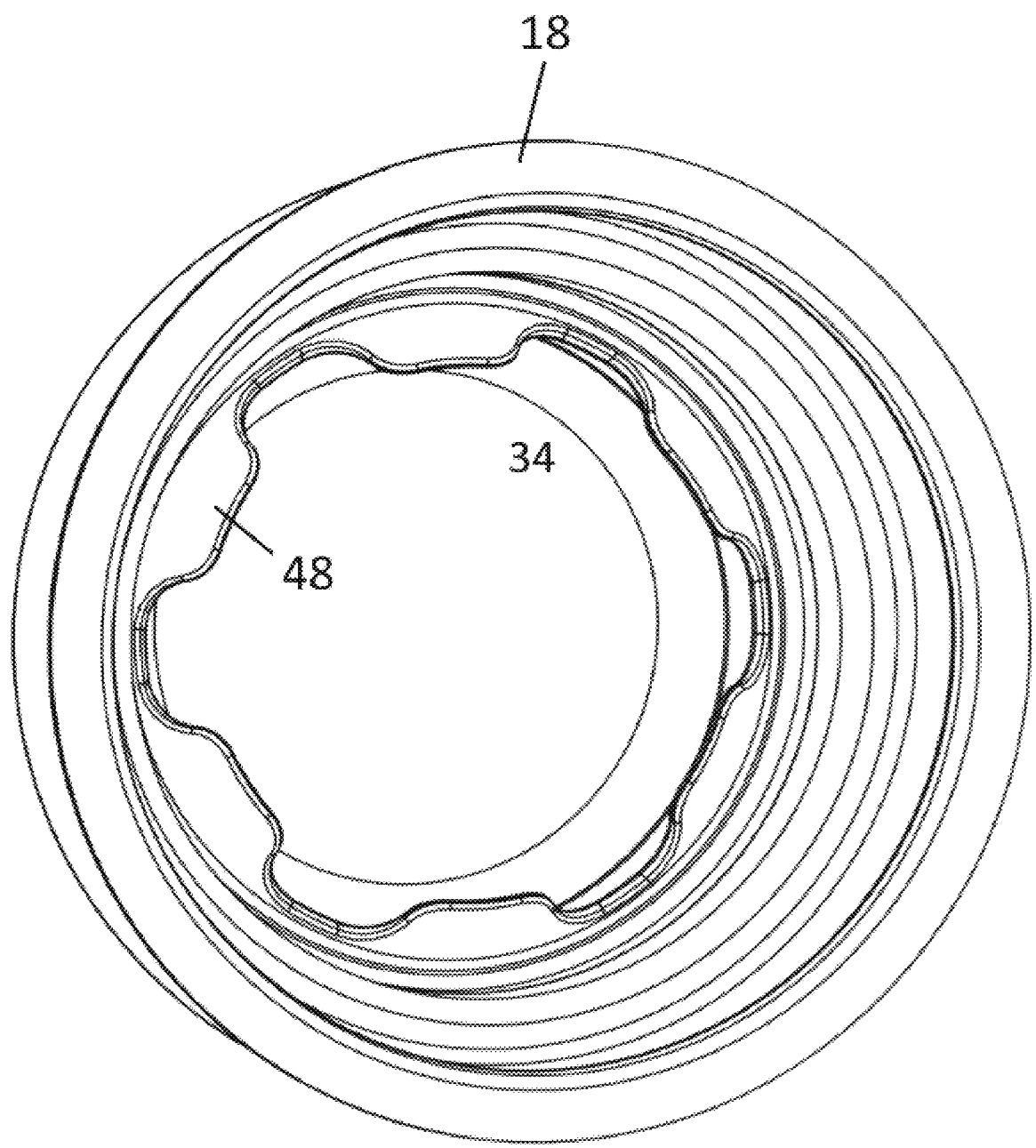
FIG. 22 is an underside view of the stack portion according to one or more embodiments of the present invention.

Performing a similar function as the ribs 82 of the lens housing 54, the tool portion 37 of the cavity 36 may be shaped and configured to engage and secure the lens 30. The tool portion (or floor) 37, the capture portion 16 and/or the stack portion 18 may include or define geometries 83 for contacting the lens 30 and securing the lens 30 into position. For example, FIGS. 23 and 26 depict a tool portion 37 shaped to engage the lens 30 at and/or proximal to an apex of the lens 30. The tool portion 37 may define a depression-shaped geometry 83 on the convex tool portion (or floor) 37 for engaging a lens 30. Other configurations may be envisioned where the geometries 83 of the tool portion 37 only engages the lens 30 proximal to a perimeter or skirt of the lens 30, such that the portion of the lens 30 designed to enhance vision is not engaged (see e.g., the geometries 83B defined by the underside of the clefts 40 of the tool portion 37 in FIG. 21). For example, turning to FIGS. 24 and 25, lens wings 48 may be defined by the capture portion 16 and/or stack portion 18 for engaging the lens 30.

The lens wings 48 may extend centrally and away from the wall portion 33. Further, each wing 48 may be shaped for contouring the contact lens 30 when the contact lens 30 is engaged by the capture portion 16. In some embodiments, at least one wing 48 may substantially form an isosceles trapezoid shape, a longest side of the wing 48 being proximal to the wall portion 33 and a shortest side of the wing 48 being distal from the wall portion 33. In some embodiments, the shortest side of the wing 48 may define a concave arc for assisting the capture, release and positioning of the contact lens 30 (e.g., FIG. 25). As one skilled in the art would realize, numerous configurations of cleft(s) 40 and wing(s) 42 may be incorporated into the structure of the capture portion 16 and/or stack portion 18.

Looking to the stack configuration generally, which is depicted at least in FIGS. 23-29, each combination of a capture portion 16 and a stack portion 18 may be arranged to selectively engage with each other into a stack configuration, so that a plurality of combination capture and stack portions 16, 18 may be shipped, stored and used together. The capture portion 16 and stack portion 18 of each combination may be unitarily constructed or may be constructed separately. The capture portion 16 may be deformable and comprised of flexible material. The stack portion 18 may be comprised of rigid material.

By using a contact lens tool 12 to engage a contact lens 30 and place the contact lens 30 onto the eye, the user advantageously is not required to touch the contact lens 30 or contact lens solution 96, thereby reducing the chance of introducing foreign matter or residue to the contact lens 30 or eye. In fact, because the contact lens 30 extends away from the contact lens tool 12 when engaged by the embodiments of the tool 12—see FIG. 3—placement of the contact lens 30 onto the eye does not require the tool 12 to contact the eye either. Further, at least a portion of the contact lens tool 12 and/or the capture portion 16 may be made of soft or flexible material, so that any contact with the eye has less of a risk of damaging the eye.

The stacking configurations of FIGS. 23-29 advantageously permit multiple contact lenses 30 to be stored with each tool 12 and/or kit 10. Through the numerous capture portion 16 and stack portion 18 configurations disclosed herein, each capture/stack combination 16/18 may be selectively engaged with each other to create a stacking configuration. These configurations ensure that the lens 30 is held into position, that each combination is coupled, and permits appropriate liquid and air flows, as desired. Regardless of whether the wall portion 33 of the cavity 36 includes the capture wall 43, the stack wall 47, or both walls 43, 47, the capture wall 43 and stack wall 47 may also be configured to nestingly couple to each other. An adhesive may be used to secure such coupling, or, in other embodiments, the two walls 43, 47 may define additional nesting features shaped to snap together and maximize the friction and alignment between the two walls 43, 47 (e.g., an female indentation and corresponding male protrusion).

Figure 4C:
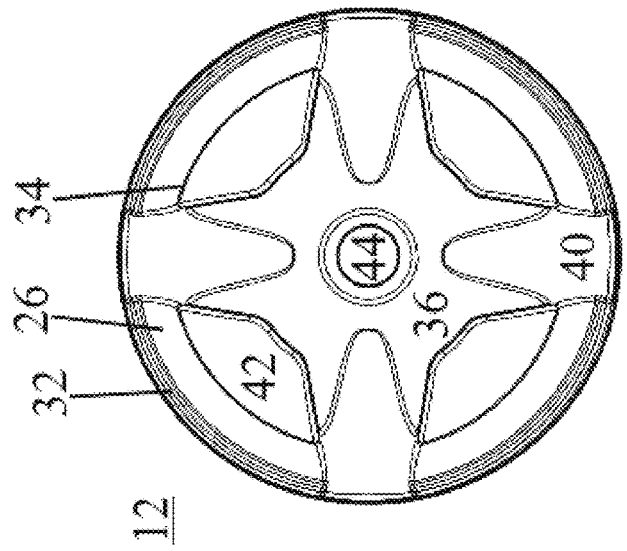
FIG. 4C is an end view of the contact lens tool including wings according to one or more embodiments of the present invention.
Figure 4B:
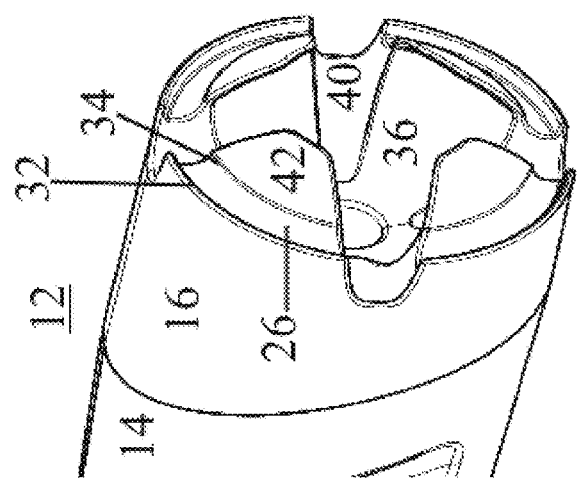
FIG. 4B is a perspective view of the contact lens tool including wings according to one or more embodiments of the present invention.
Figure 4A:
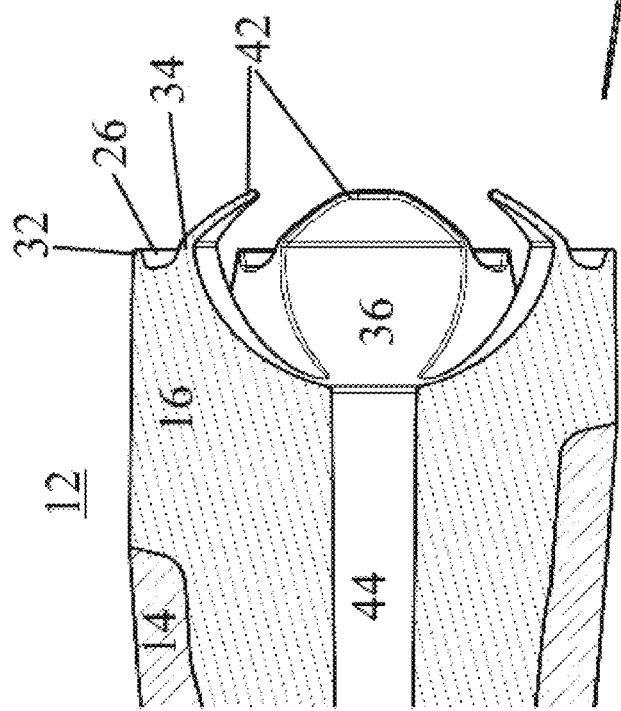
FIG. 4A is a cross-section view of the contact lens tool including wings according to one or more embodiments of the present invention.

According to at least one embodiment, the capture portion 16 may further define at least one cleft 40 and/or wing 42. For example, the capture portion 16 may include at least two clefts 40 positioned opposite from each other and extending centrally through the groove 26 and/or outer edge 32 to the cavity 36. In the embodiments of FIGS. 2A and 4A-4C, two pairs of clefts 40 are defined, with each cleft 40 of each pair positioned opposite the other cleft 40 of the same pair. The shape of the cleft 40 may extend within the cavity 36 from the outer edge 32, as depicted in FIG. 4C.

According to at least one embodiment, the capture portion 16 may further define at least one wing 42 for supporting the contact lens 30 when the contact lens 30 is engaged with the contact lens tool 12. The additional frictional contact between the contact lens tool 12 and the contact lens 30 by any wing(s) 42 aids the groove 26 and/or outer edge 32 in preventing displacement or deformation of the contact lens 30 when in storage within the contact lens tool kit 10, when the liquid solution 96 is drained, and/or when the contact lens 30 is being placed on the eye by the contact lens tool 12. At least one wing 42 may be advantageous when the contact lens tool 12 is being used with thinner contact lenses 30 by offering greater support and frictional contact to the contact lens 30—a thinner contact lens 30 has an increased probability of deforming or displacing when in storage or use.

In the embodiments of FIGS. 4A-4C, 12, 15 and 16, four wings 42 are defined by the capture portion 16. In some embodiments, each wing 42 extends centrally and away from the outer edge 32 and/or the interior rise 34. When clefts 40 are defined by the capture portion 16, at least one wing 42 may be positioned between the clefts 40. Further, each wing 42 may be shaped for contouring the contact lens 30 when the contact lens 30 is engaged by the contact lens tool 12. In some embodiments, at least one wing 42 may substantially form an isosceles trapezoid shape, a longest side of the wing 42 being proximal to the rise 34 and a shortest side of the wing 42 being farthest from the rise 34. In some embodiments, the shortest side of the wing 42 may define a concave arc for assisting the capture, release and positioning of the contact lens 30 (e.g., FIG. 12).

As one skilled in the art would realize, numerous configurations of cleft(s) 40 and wing(s) 42 may be incorporated into the structure of the capture portion 16 of the contact lens tool 12. For example, a single wing 42 may be defined by the capture portion 16, the single wing 42 being shaped like a convex cavity 36 and having one or more pores located thereon for fluid flow therethrough. Various porous designs may be provided. Further, any cleft(s) 40 and/or wing(s) 42 may be made of varying materials of a wide range of thicknesses, whether rigid or soft, coarse or smooth, permeable or non-permeable. As noted herein, flexibility of any wing(s) 42 may help to reduce potential damage or irritation to the eye during placement of a contact lens 30 using the contact lens tool 12. Similarly, thinner wings 42 may be desirable to minimize abrasive contact with the eye when the contact lens tool 12 is in use.

According to at least one embodiment, the capture portion 16 may be shaped to invert the contact lens 30 upon engagement therewith. For example, the rise 34, wing(s) 42 and/or a convex cavity 36 may work in conjunction with a lens housing 54 to invert the lens 30 and engage the contact lens tool 12 with the lens 30.

Figure 6:
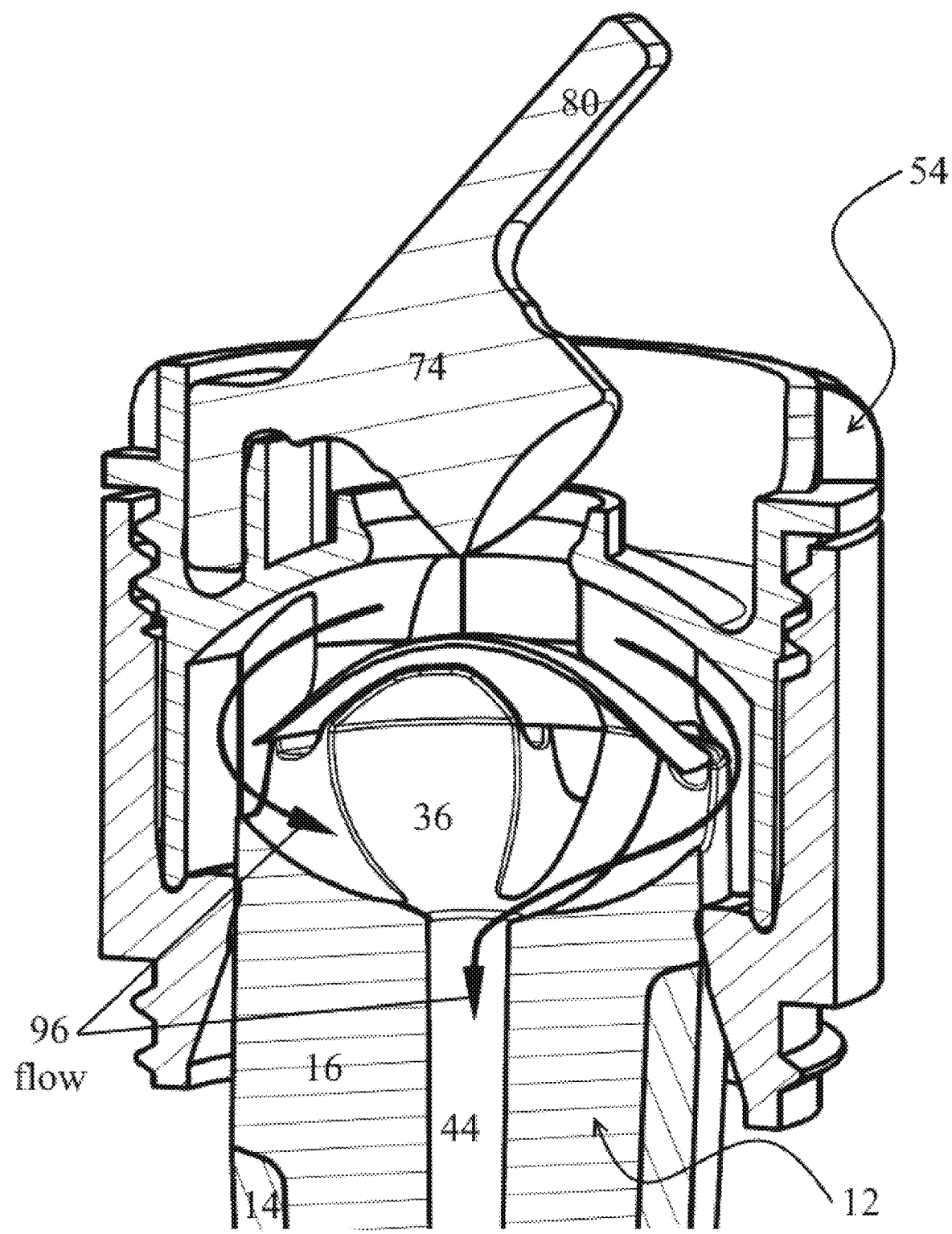
FIG. 6 is a cross-section of the contact lens tool kit in operation according to one or more embodiments of the present invention.
Figure 7:
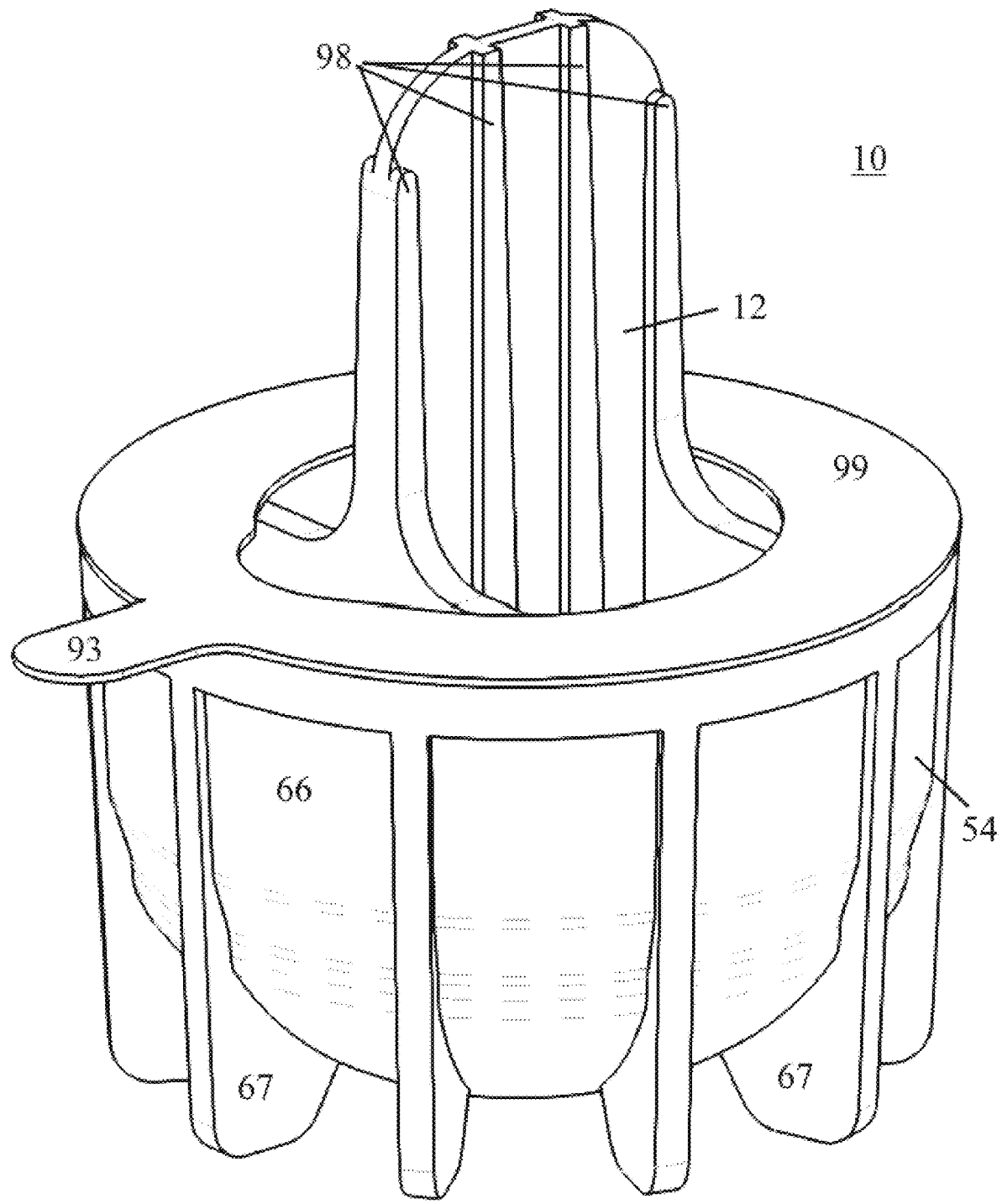
FIG. 7 is a perspective view of the contact lens tool kit including a housing seal and tab handle portion according to one or more embodiments of the present invention.

According to some embodiments, the capture portion 16 of the tool 12 may further define at least one aperture 44 for permitting fluid flow therethrough. For example, turning to FIGS. 1 and 6, the aperture 44 may extend from the cavity 36 along the length of the contact lens tool 12 to an opening 46 for permitting fluid flow from the cavity 36 to the opening 46 and vise versa. Some embodiments of the aperture 44 include the added advantage of a user being able to visually align placement of the contact lens 30 during use; this visual alignment encourages consistent and accurate placement of the contact lens 30 onto the eye by the contact lens tool 12.

According to at least one embodiment of the present invention, the contact lens tool 12 may include a handle portion 14 at least partially covering the exterior of the capture portion 16. The handle portion 14 may be securely coupled or releasably engaged to the capture portion 16. Further, the handle portion 14 may define an opening 46 engaged with the capture portion 16 or the aperture 44 of the capture portion 16 for permitting fluid flow through the opening 46 and/or the aperture 44. As one skilled in the art would appreciate, the handle portion 14 may include grooves, coarse treatments, and/or gripping elements on its surface for providing improved handling of the contact lens tool 12 during use. Further the handle may be made of rigid and/or soft materials. For example, the handle 14 may include missing portions, thereby exposing the capture portion 16 underneath, the capture portion extending through the exposed portions for providing a gripping element for the user. In the embodiment of FIG. 2A, an elongated indent is defined by the handle 14 for providing greater accuracy during manipulation of the contact lens tool 12. In the embodiment of FIG. 2B, two smaller indentions are defined by the handle 14 for improved handling of the contact lens tool.

According to embodiments, the tool housing 52 may define a tool exterior 56 and a tool base 60 positioned on one end of the tool exterior 56. The tool base 60 may define a pole 62 extending within the tool exterior 56 for selectively engaging the contact lens tool 56. The pole 62 may engage the aperture 44 and/or opening 46. Engagement of the aperture 44 and/or opening 46 by the pole 62 may seal the aperture 44 and/or opening 46 such that fluid flow is not permitted therethrough.

The tool housing 52 may further define at least one protrusion 94 extending within the tool exterior 56 for supporting the contact lens tool 12 when engaged with the tool housing 52. For example, as depicted in FIG. 1, an annular protrusion 94 may extend from the tool base 60, thereby providing a recess in which the contact lens tool 12 may be housed and supported. By supporting the contact lens tool 12, the at least one protrusion 94 may help maintain the correct positioning of the contact lens tool 12 relative to the contact lens 30, a ledge 84, and/or the pole 60.

In FIGS. 5A-5C, a lens housing 54 defining a lens base 70 on one end is depicted. The lens base depicted in FIG. 5A includes gripping features 98 on the surface to aid the user in manipulating the lens housing 54. In FIGS. 7-9 and 11-12, the tool 12 may define one or more gripping features 98 on the surface of the handle portion 14 of the tool 12 for aiding the user in gripping and manipulating the tool 12. The tool 12 of FIGS. 7-9 and 11-12 includes a substantially tab handle portion 14 that is substantially flat and defines gripping features 98 thereon. The gripping features 98 may be two or more substantially parallel ridges running the length, or a portion thereof, of the handle portion 14 of the tool 12.

The cross section view of FIG. 5B depicts a lens housing including a plug 74 for releasing fluid therein. The plug 74 may be releasably engaged with the lens housing 54 or may be securely coupled to the lens housing 54 or both. For example, a plug cavity 52 may be defined by the lens housing 54 for coupling the plug 74 to the lens housing 54. Additionally, plug aperture 76 may be defined by the lens housing 54 for selectively engaging the plug 74. Additionally, the plug may define a plug lip 80 for permitting a user to easily manipulate the plug 74 to, for example, selectively engaging the plug 74 with the plug aperture 76. As depicted in FIGS. 5A and 5B, the plug 74 may have a substantially flat surface so that, when coupled and/or engaged with the lens housing 54, the lens housing may lay flat on a surface in contact with the lens base 70 end of the lens housing 54.

In embodiments where the plug 74 is selectively engaged with a plug aperture 76, the plug may extend a distance past the plug aperture 76 of the lens base for supporting a contact lens 30 when housed within the lens housing 54. Further, the portion of the plug 74 extending through the plug aperture 76 may be shaped to conform to the shape of a contact lens 30. The surface of the plug 74 supporting the contact lens 30 may include surface indentations or be coarse in nature or involve other physical features in order to minimize the surface tension between the contact lens 30 and plug 74. For example, the plug 74 may include clefts similar to the capture portion 16 and/or may include an annular rise similar to the capture portion 16, where the interior portion of the surface of the plug 74 has a greater concavity than the lens 30 such that only the annular rise is in contact with the lens 30. In most embodiments of the plug 74, when the plug is disengaged from the aperture 76 of the lens housing 54, the disengagement reduces the adhesion between the contact lens 30 and the lens housing 54, thereby permitting easier removal of the contact lens 30 by the lens tool 12. For example; a plug 74 supporting a contact lens 30 will create adhesion between the two when in contact; disengagement of the plug 74 removes these adhesive properties.

The lens base 70 may define at least one rib 82 for receiving and/or supporting the contact lens. For example, the lens base 70 may define a plurality of ribs 82 extending centrally within the lens housing 54 for receiving the contact lens 30; as depicted in FIGS. 5B and 5C. As one skilled in the art would appreciate, numerous rib 82 configurations are available to serve at least one purpose of receiving a contact lens 30; supporting the contact lens 30 to prevent deformation or improper settlement of the contact lens 30, minimizing surface tension between the contact lens 30 and any rib(s) 82 for easier removal from the lens housing, and suspending the contact lens 30 in a liquid solution 94 so that foreign objects may settle without contact with the contact lens 30. One example may include ribs 82 shaped to conform to the shape of the contact lens 30. Another embodiment may include the ribs 82 working in conjunction with the plug 74. Yet another embodiment may include at least one rib 82 extending across the entire width of the lens base 70, such that each rib 82 engages the lens 30 through a finite number of contact points.

Figure 10:
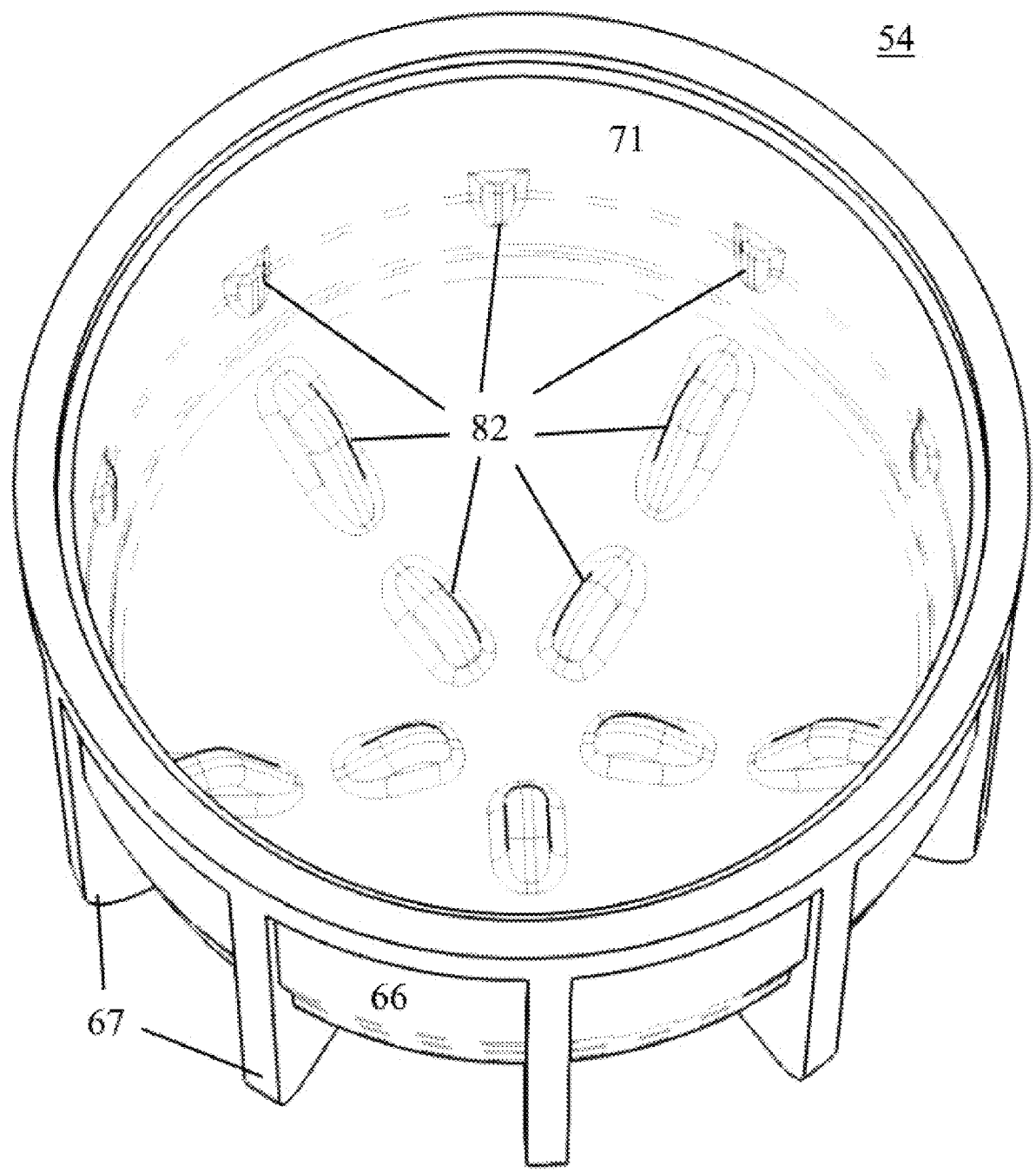
FIG. 10 is a perspective view of the contact lens housing according to one or more embodiments of the present invention.

One embodiment of the ribs 82 defined by the lens housing 54 is depicted in FIG. 10. A plurality of ribs 82 may be defined about the lens interior 71 of the lens housing 54. The ribs 82 may be shaped similarly to a triangular prism, for example. Additional ribs may be defined by the lens base 70. In FIG. 10, a first group of ribs is spaced about a first circle about the base 70 and a second group of ribs is spaced about a concentric second circle about the base 70. Some or all of the ribs 82 may be shaped to include an apex point and/or apex ridge for contacting the contact lens 30 and granting separation between the lens 30 and the base 70 and/or interior 71 of the lens housing 54.

As depicted in FIG. 5C, the lens housing 54 may define a lens base 70 and further include a drain seal 97 and/or housing seal 99. The lens housing 54 may be capable of storing a contact lens 30 suspended in a liquid solution 96 therein. A lens housing 54 having a drain seal 97 and/or housing seal 99 may additional include any of the features described herein, alone or in combination, such as various configurations of ribs 82, a ledge 84, and gripping features 98. The drain seal 97 and/or housing seal 99 may be a flexible membrane, and may be removable and/or frangible. A contact lens tool kit 10 having a lens housing 54 including a housing seal 99 may also include a tool housing 52 having a plug 74 and/or a tool 12 having a plug 74. The embodiments where the lens housing 54 includes a housing seal 99 may be used to package and store one-time-use contact lenses 30. Drainage of the liquid solution 96 from the lens housing 54 may be performed using the drain seal 97, a plug 74 engaged and/or coupled with the tool 12, and/or a plug 74 engaged and/or coupled with a tool housing 52. The method of using a lens housing 54 with a drain seal 97 and/or housing seal 99 in conjunction with other components of the contact lens tool kit 10 is further described herein.

Figure 8:
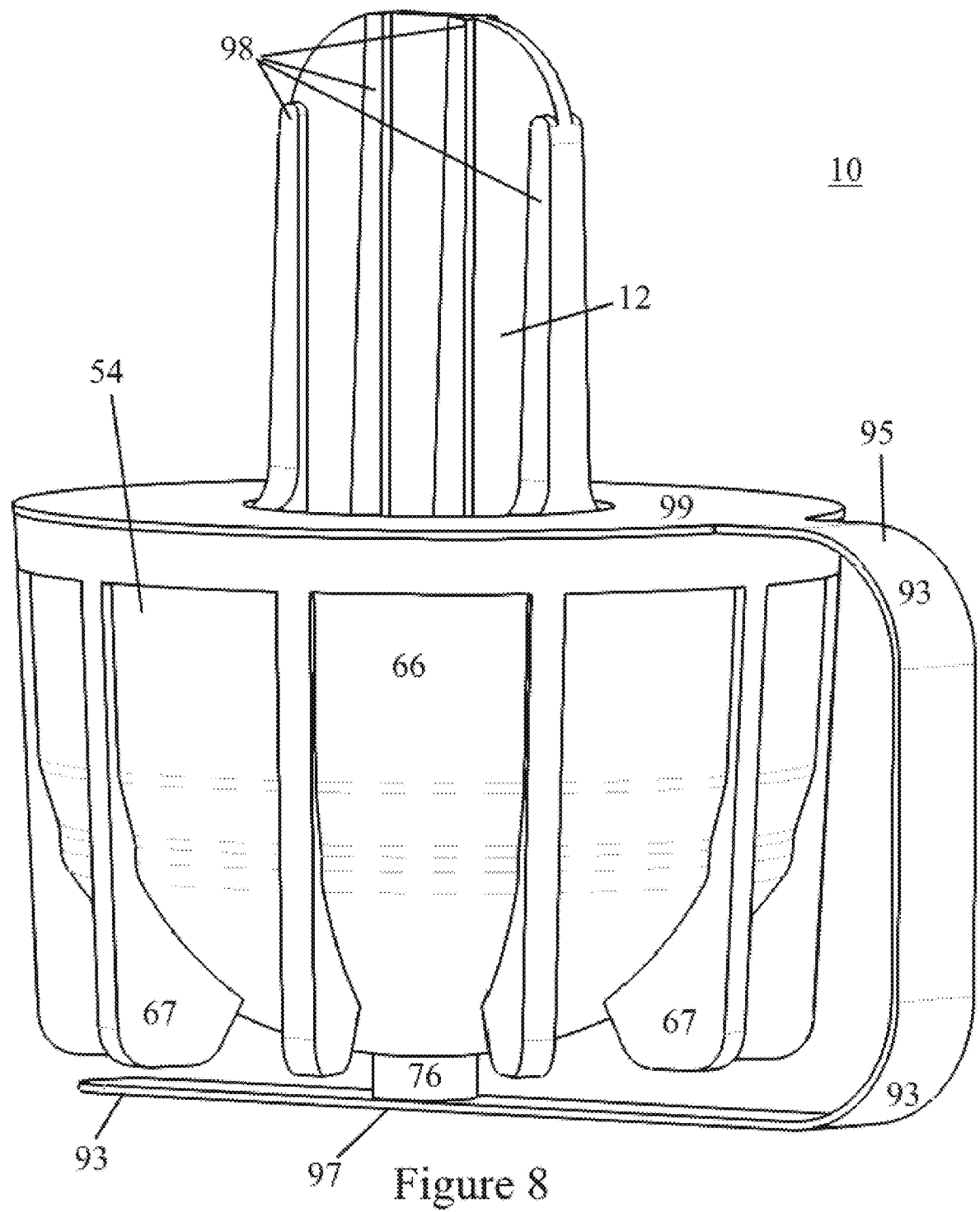
FIG. 8 is a perspective view of the contact lens tool kit including a combination seal and a tab handle portion according to one or more embodiments of the present invention.

In other embodiments, such as FIG. 8, a combination seal 95 may be provided for sealing both the plug aperture 76 extending from the base of the lens exterior 66 using a drain seal 97 and for sealing any gap between the tool 12 and the lens housing 54 using a housing seal 99. For example the gap may be between the handle portion 14 of the tool 12 and the interior 71 of the lens housing 54. Notably, the housing seal 99 may include a seal aperture 91 through which the handle portion 14 of the lens tool 12 may extend (e.g., FIGS. 7-8), A tab 93 may extend from any seal 95, 97, 99 described herein for easy removal of the seal 95, 97, 99. The seal 95, 97, 99 may be tearable or may be constructed to remain unitary when removed. The seal 95, 97, 99 may include foil and/or an adhesive. The combination seal 95 may include a tab 93 extending between, and adjoining, the housing seal 99 and the drain seal 97 (e.g., FIG. 8). The tab 93 extending between, and adjoining, the housing and drain seal 99, 97 may extend outward from the exterior 66 or may run along the surface of the exterior 66. In one embodiment, the tab 93 may run along the surface of a lens housing ridge 67. The tab 93 may have a width greater than the lens housing ridge 67 for easy manipulation of the tab 93. Alternatively, the ridge 67 may define a divot over which the tab 93 extends for easy manipulation of the tab 93.

In other embodiments, the lens housing 54 may be capable of engagement with a capture portion 16 of a lens tool 12 such that the engagement is impermeable to fluid flow. In such an embodiment, the liquid solution 96 and lens 30 may be stored in the lens housing 54 while engaged with the capture portion 16. Disengagement of the capture portion 16 from the lens housing 54, whether by direct disengagement of the tool 12 or by indirect disengagement through selective engagement of a handle portion 14 with the capture portion 16 of the tool 12, thereby removes the lens 30 from the lens housing 54. In one embodiment, the engagement of the handle 14 with the capture portion 16 may enlarge an aperture 44 in the capture portion 16 or break a frangible seal on the aperture 44 of the capture portion, thereby aligning the aperture 44 with the opening 46 of the handle for draining the liquid solution 96 from the lens housing 44. Alternatively, a drain seal 97 located on the lens housing 44 may be removed or broken for draining.

According to some embodiments, the lens housing 54 may further define a ledge 84 extending centrally for supporting engagement of the contact lens tool 12 when the lens housing 54 and tool housing 52 are engaged or when the contact lens tool 12 is attempting to engage the contact lens 30 received by the lens housing 54. As depicted in FIGS. 5B and 5C, the ledge 84 may be shaped with a taper and/or curve to provide varying engagement with the contact lens tool 12.

For manufacturing purposes, the lens housing 54 may be constructed using two components that are securely engaged with each other. The lens housing may be impermeable to fluids or liquid fluids. The tool housing may include tool housing engagements 64. The lens housing may include lens housing engagements 92. Both engagements 64, 92 may be configured so that fluids or liquid fluids may not flow therebetween when engaged with each other. Engagement of the tool housing 52 with the lens housing 54 may be impermeable to fluids or liquid fluids.

According to at least one embodiment, a method of engaging a contact lens 30 with a contact lens tool 12 is provided. The method may include the step of providing a contact lens tool kit 10 according to any embodiments described herein. For example, the contact lens tool kit 10 may include a tool housing 52, a lens housing 54 and a contact lens tool 12. Alternatively, the method may require a lens housing 54 and a contact lens tool 12, without the need for a tool housing 52. A step of the method may include pouring a liquid solution 96 into a lens housing 54. A contact lens 30 may then be inverted and placed in the liquid solution 96 of the lens housing 54. Alternatively, the lens 30 may be placed in the liquid solution 96 without being inverted, allowing for a contact lens tool 12 to invert the contact lens 30 upon engagement. The lens housing 54 may be any embodiment described herein or, alternatively, may be a contact storage case traditionally used in the prior art. A step of the method may include inserting the contact lens tool 12 into the lens housing 54, thereby engaging the contact lens tool 12 with the contact lens 30 and the lens housing 54. FIG. 3 depicts the contact lens tool 12 in engagement with the contact lens 30.

According to some embodiments, a method may include providing a lens housing 54 with at least one lens seal 99. The lens housing 54 may contain therein a contact lens 30 suspended in liquid solution 96. The contact lens 30 may be either inverted or not-inverted when in suspension. The method may include removing or breaking a seal 99 from the lens housing 54. The seal 99 may be removed for subsequent engagement of the lens housing 54 with either a lens tool 12 or tool housing 52. Alternatively, engagement of the lens housing 54 with the lens tool 12 or tool housing 52 may cause the lens seal 99 to break, thereby allowing fluid flow therebetween. Once the lens housing 54 is engaged to either the lens tool 12, the tool housing 52 or both, a second lens seal 99 may be removed or broken for draining the liquid solution 96 from the lens housing 54. Alternatively, a plug 74 positioned on the tool 12 and/or tool housing 52 may be disengaged for draining the liquid solution 96.

In at least one embodiment, a method may include the step of a tool 12 engaging a lens housing 54, thereby breaking a frangible seal 99 of the lens housing 54 engaging a contact lens 30 housed therein. A plug 74 may then be removed from the aperture 44 of the tool 12 for draining the liquid solution 96 in which the contact lens 30 is suspended. In one embodiment, the lens housing 54 defines at least one rib 82 for supporting a non-inverted lens 30 such that engagement of the lens housing 54 with the tool 12 involves at least one wing 42 inverting the contact lens 30 with support of the at least one rib 82.

As described herein, various features of the contact lens tool kit 10 may aid in providing alignment and support to the contact lens tool 12 for proper engagement with the contact lens 30. For example, the interaction of the tool 12 with the ledge 84 may help ensure that the tool 12 aligns with the contact lens 30. Additionally, the ribs 82 and/or plug 64 may help ensure that the contact lens 30 is properly positioned for engagement within the lens housing 54. When using the tool housing 52 as well, the pole 62 and/or the protrusion 94 may help ensure proper positioning.

In some embodiments, the method of using the tool 12 and/or kit 10 may include the placement of a lens 30 upon a user's eye when the lens 30 has been stored in a stacking configuration. The stacking configuration may include two or more lenses 30 each engaged with a corresponding capture portion 16. Each capture portion 16 may be coupled to a corresponding stack portion 18. In the stacking configuration of FIG. 23, the contact lens 30A may be placed upon the user's eye, thereby deforming the lens portion 38 and expelling air through the cleft 40. Meanwhile, there may remain fluid stored between the stack portion 18A and the adjacent capture portion 16B which had been preserving the lens 30B. To access the lens 30B, the stack portion 18A may be disengaged from the capture portion 16B. In some embodiments, such as FIG. 26, a configuration seal 59 may be wrapped about an exterior of the stack edge 49A and stack edge 49B for sealing a stack edge aperture 53. The seal 59 may be adhered to the edges 49A, 49B using an adhesive. Once the seal 53 is removed, fluid may drain through the stack edge aperture 53 and the stack portion 18A may be disengaged from the capture portion 16B.

Figure 27:
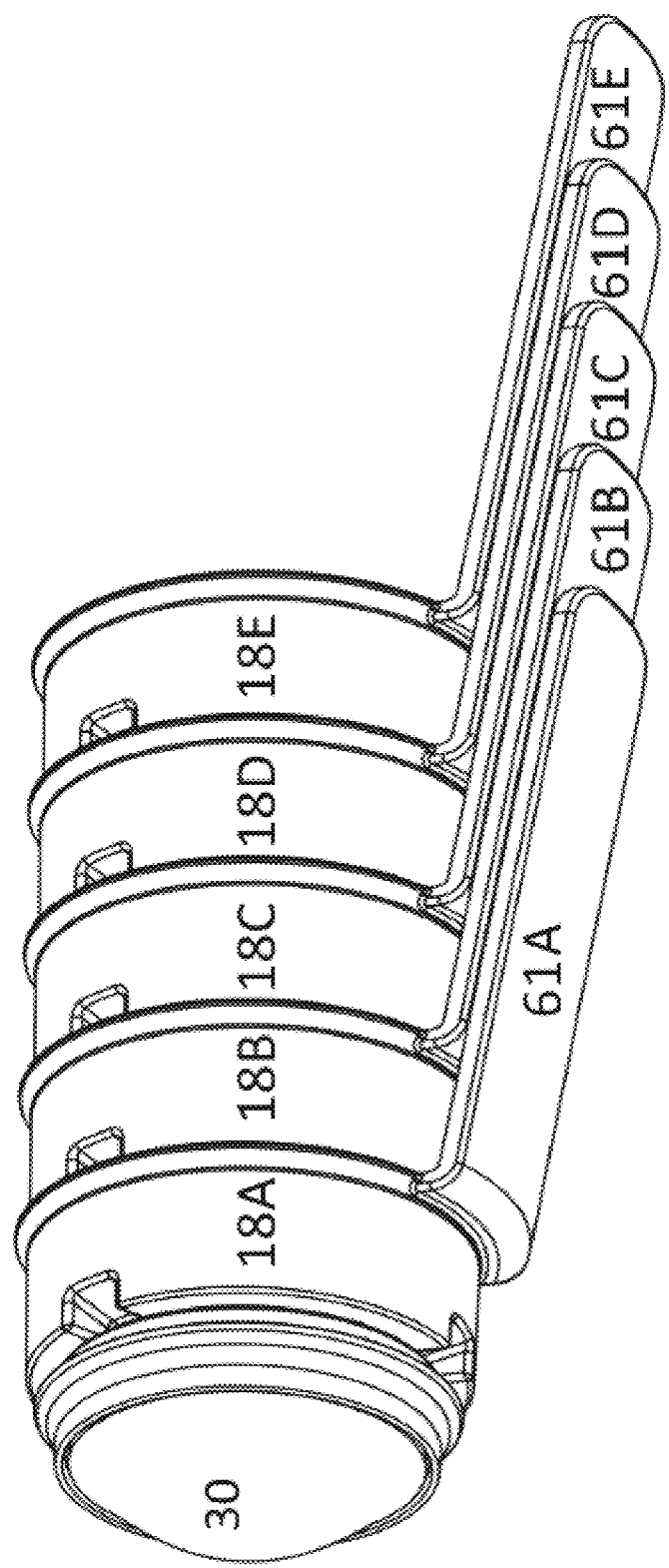
FIG. 27 is a perspective view of a stacking configuration of capture portion and stacking portions having a stack handle according to one or more embodiments of the present invention.

FIG. 27 depicts an embodiment of the stack portion 18A which includes a stack handle 61 for easing disengagement of the stack portions 18A, 18B from each other.

According to at least one embodiment, the method may include providing a tool housing 52, wherein the step of inserting the contact lens tool 12 into the lens housing 54 may involve engaging the tool housing 52 with the lens housing 54. In method embodiments wherein both a lens housing 54 housing a contact lens 30 and a tool housing 52 housing a lens tool 12 are involved, engagement of the lens housing 54 with the tool housing 52 causes engagement of the lens tool 12 with the contact lens 30. When the tool housing 52 and lens housing 54 are disengaged, the lens tool 12 may be removed with the contact lens 30 engaged thereto. After the contact lens 30 is engaged by the contact lens tool 12, in any embodiment described herein, a user may then conveniently insert the contact lens 30 onto the eye 19.

According to at least one embodiment, a lens housing 54 is provided and includes a plug 64. The method may include disengaging the plug 64 from the lens housing 54, thereby releasing the liquid solution 96 from the lens housing. Subsequently, the contact lens tool 12 may be removed from the lens housing 54, thereby removing the contact lens 30 engaged to the contact lens tool 12. Alternatively, before disengaging the plug 64, the method may also include disengaging the tool housing 52 from the lens housing 54 such that the contact lens tool 12 remains engaged with the lens housing 54.

According to some embodiments, a lens 30 is stored within a liquid solution 96 within a lens housing 54. The lens housing 54 may be engaged to both a tool housing 52 and a contact lens tool 12. The tool housing 52 may be disengaged from the lens housing 54, the lens tool 12 remaining engaged with the lens housing 54. The contact lens 30 may remain suspended in the liquid solution 96, which remains in the lens housing 52. The lens housing 52 and the contact lens tool 12 may together be lifted, inverted, and relocated within risk of the liquid solution 96 escaping the confines of the lens housing 52 and/or the aperture 44 of the tool 12. Due to the surface tension of the liquid solution 96 in the aperture 44, the liquid solution 96 does not flow even when the aperture 44 and/or opening 46 is directed downward, with the contact lens 30 and solution 96 primarily positioned above the aperture 44 and/or opening 46. When positioned so, the plug 64 may be disengaged from the lens housing 44 and the solution 96 may flow through the aperture 44 and/or opening 46, thereby draining the solution 96 from the lens housing 44. Once the solution has been drained, the contact lens tool 12 may be disengaged from the lens housing 44, with the lens 30 engaged to the tool 12 for placement on the eye.

As described herein, several features of the present invention may be included to aid either the flow of the solution 96 during draining and/or the flow of air through the tool 12 during placement. For example, the aperture 44 and/or opening 46 may have a diameter or width necessary for maintaining a desired surface tension on the solution 96 contained therein. Further, the aperture 44 and/or opening 46 permits liquid flow during drainage and air flow during placement of the contact lens on the eye. Notably, when the capture portion 16 is inserted into the lens housing 54, the liquid solution 96 is displaced and therefore displaces gases contained within the lens housing 54 without the lens housing 54. In some embodiments, the engagement of the lens tool 12 with the lens housing 54 causes any gas within the lens housing to displace without the lens housing 54, thereby creating a gas-free, fluid-only volume within the lens housing 54 for storage of the contact lens 30. Additionally, the ribs 82, plug 74, plug aperture 76, cavity 36, cleft(s) 40, and/or wing(s) 42 may also work along, or in combination to provide liquid and air flows during drainage, engagement, inversion and/or placement.

Figure 28:
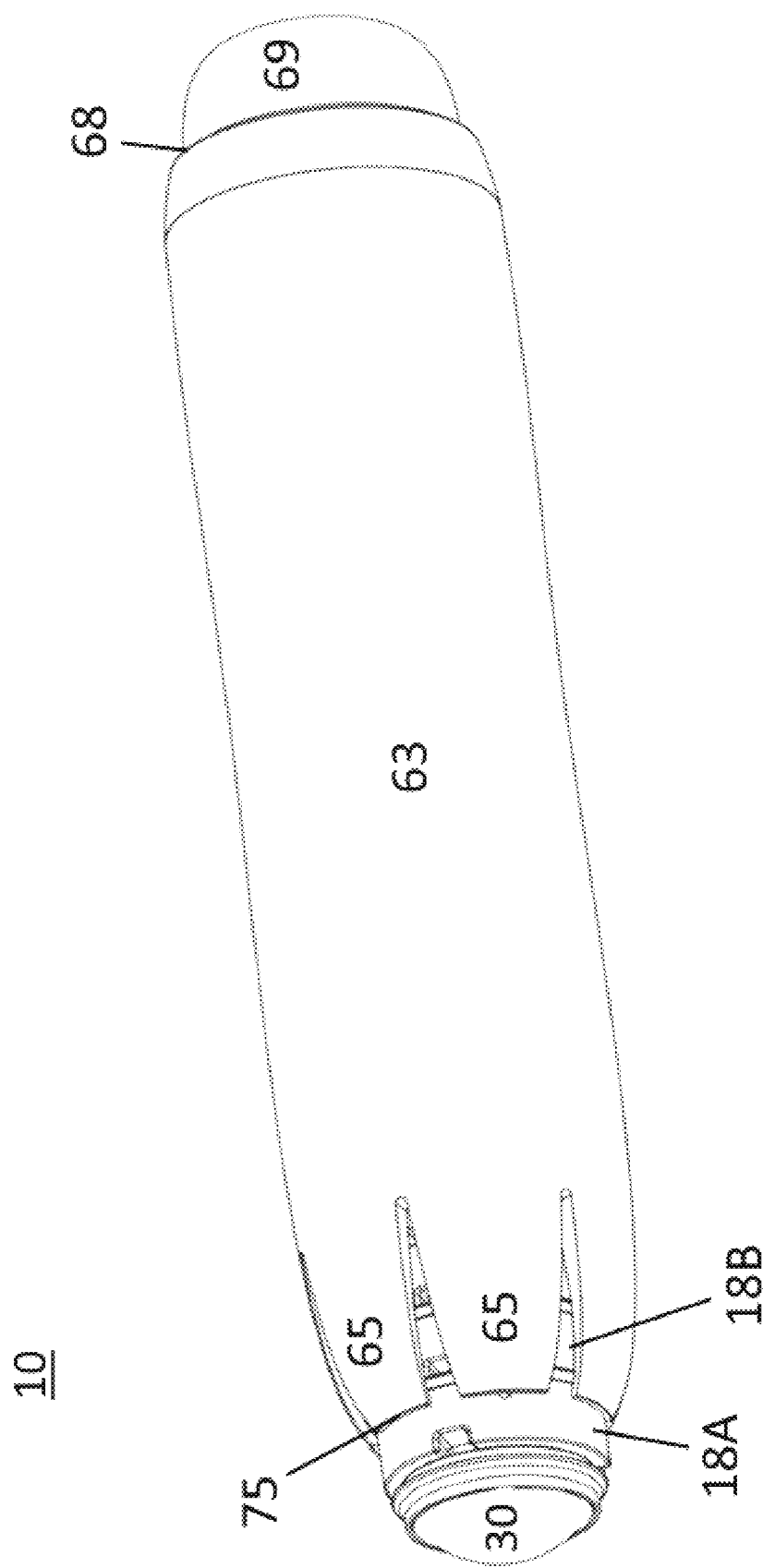
FIG. 28 is a perspective view of the contact lens tool with an extended handle portion for housing a stacking configuration according to one or more embodiments of the present invention.
Figure 29:
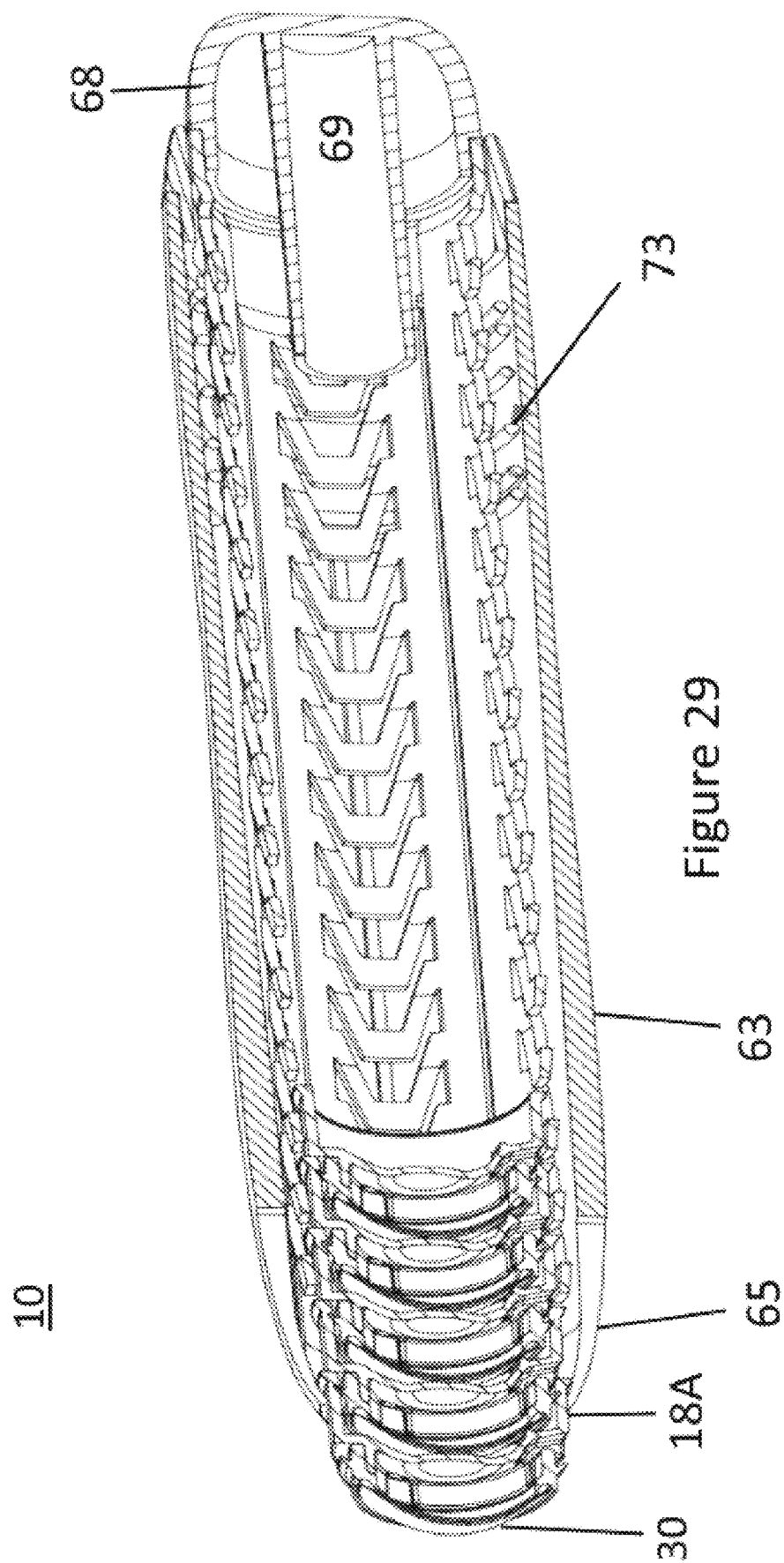
FIG. 29 is a cross-sectional view of the contact lens tool with an extended handle portion for housing a stacking configuration according to one or more embodiments of the present invention.

FIGS. 28 and 29 depict embodiments of the invention wherein the contact lens tool kit 10 and/or tool 12 further include a stack container 63 for housing a plurality of capture and stack portions 16, 18. The stack container 63 may define a plurality of stack arms 65 for selectively engaging on of the stack portions 18A. The stack container 63 may include a management end 68, which may define a button or other activator 69 for activating the container spring 73 and/or other mechanism and expelling the stack portion 18A from an open end 75 of the stack container 63.

Figure 30:
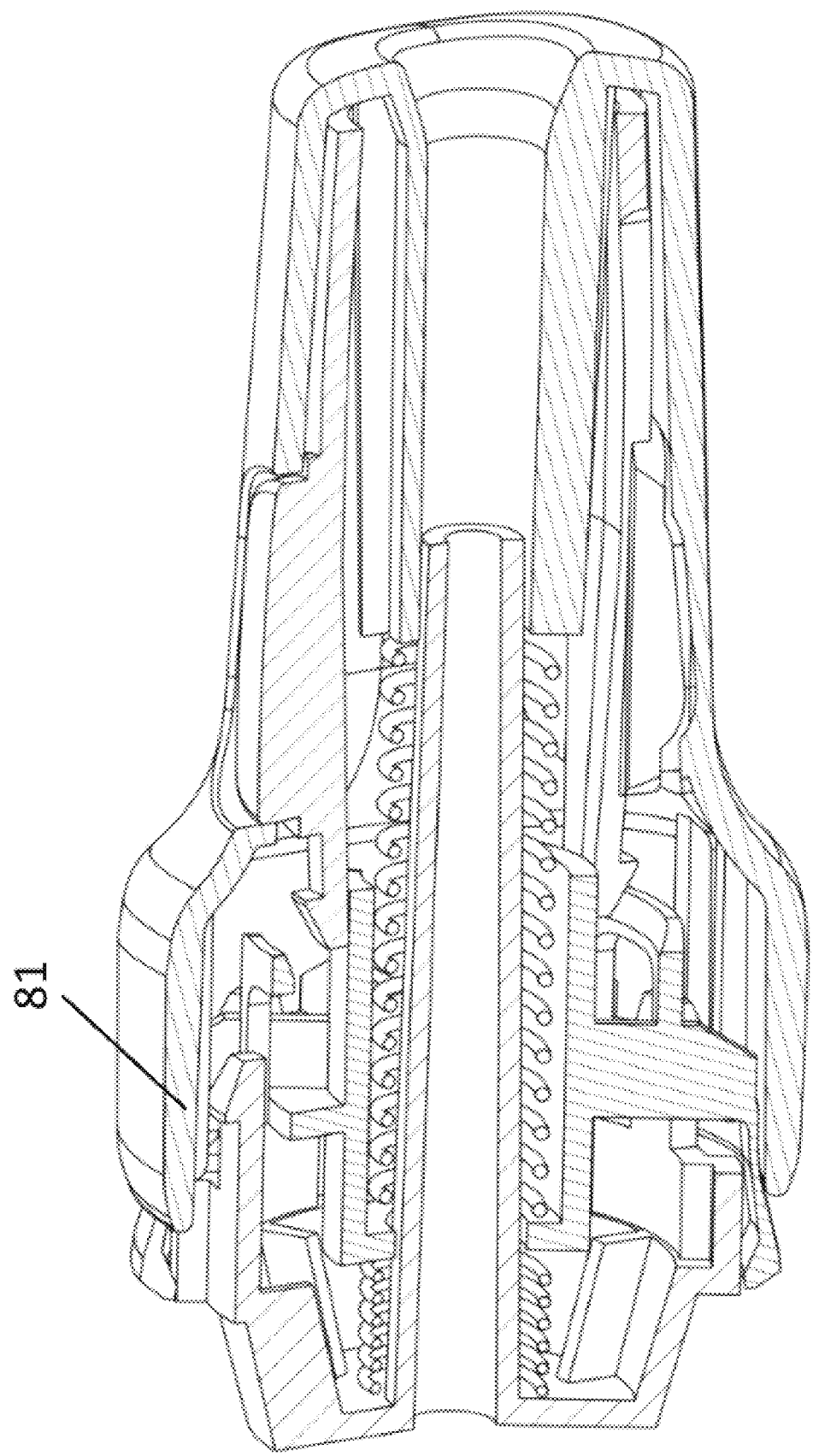
FIG. 30 is a cross-sectional view of the contact lens tool including a gripper for selectively engaging a stacking portion or capture portion according to one or more embodiments of the present invention.
Figure 31:
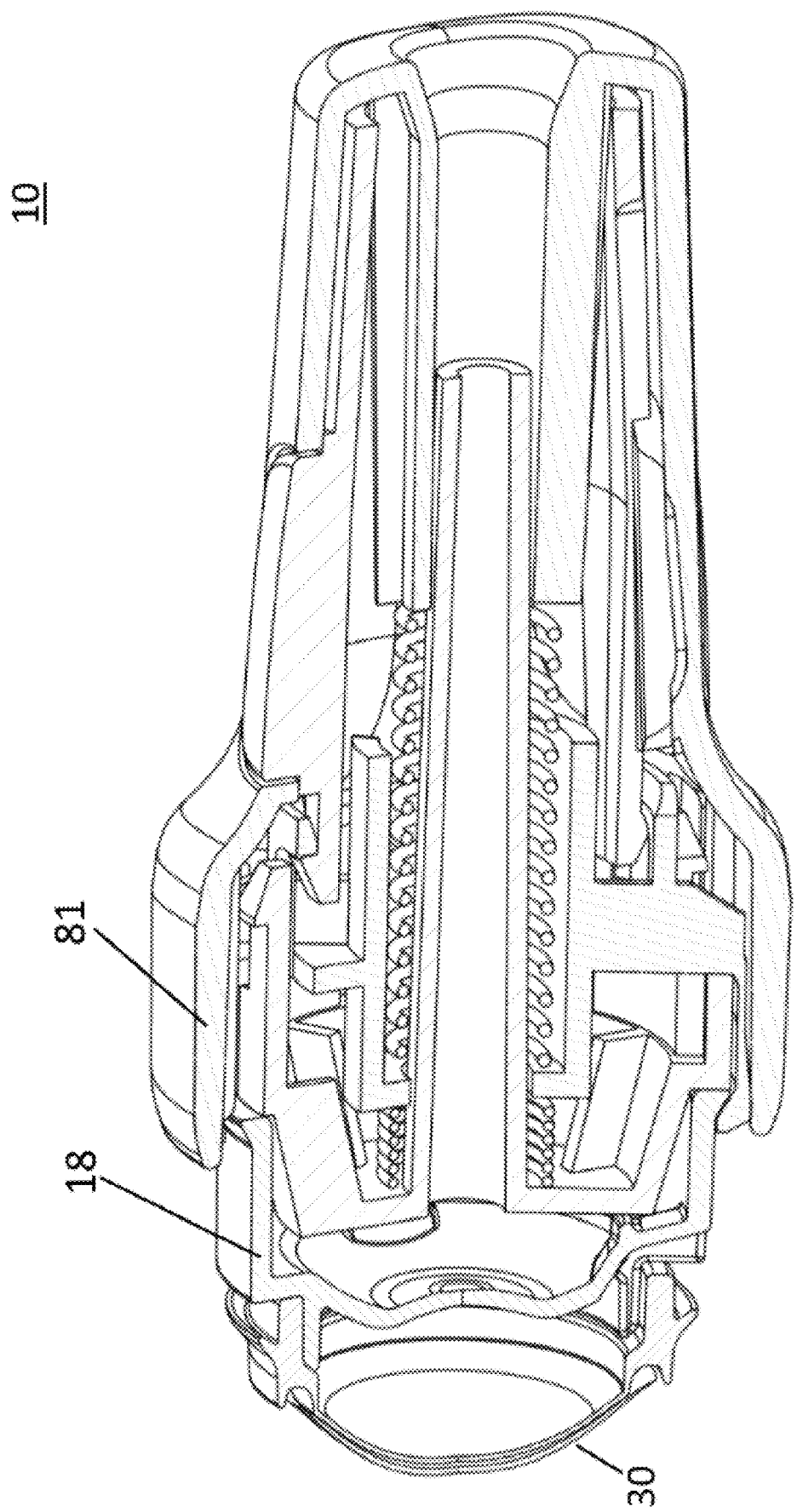
FIG. 31 is a cross-sectional view of the contact lens tool including a gripper, stacking portion, capture portion and lens according to one or more embodiments of the present invention.
Figure 32:
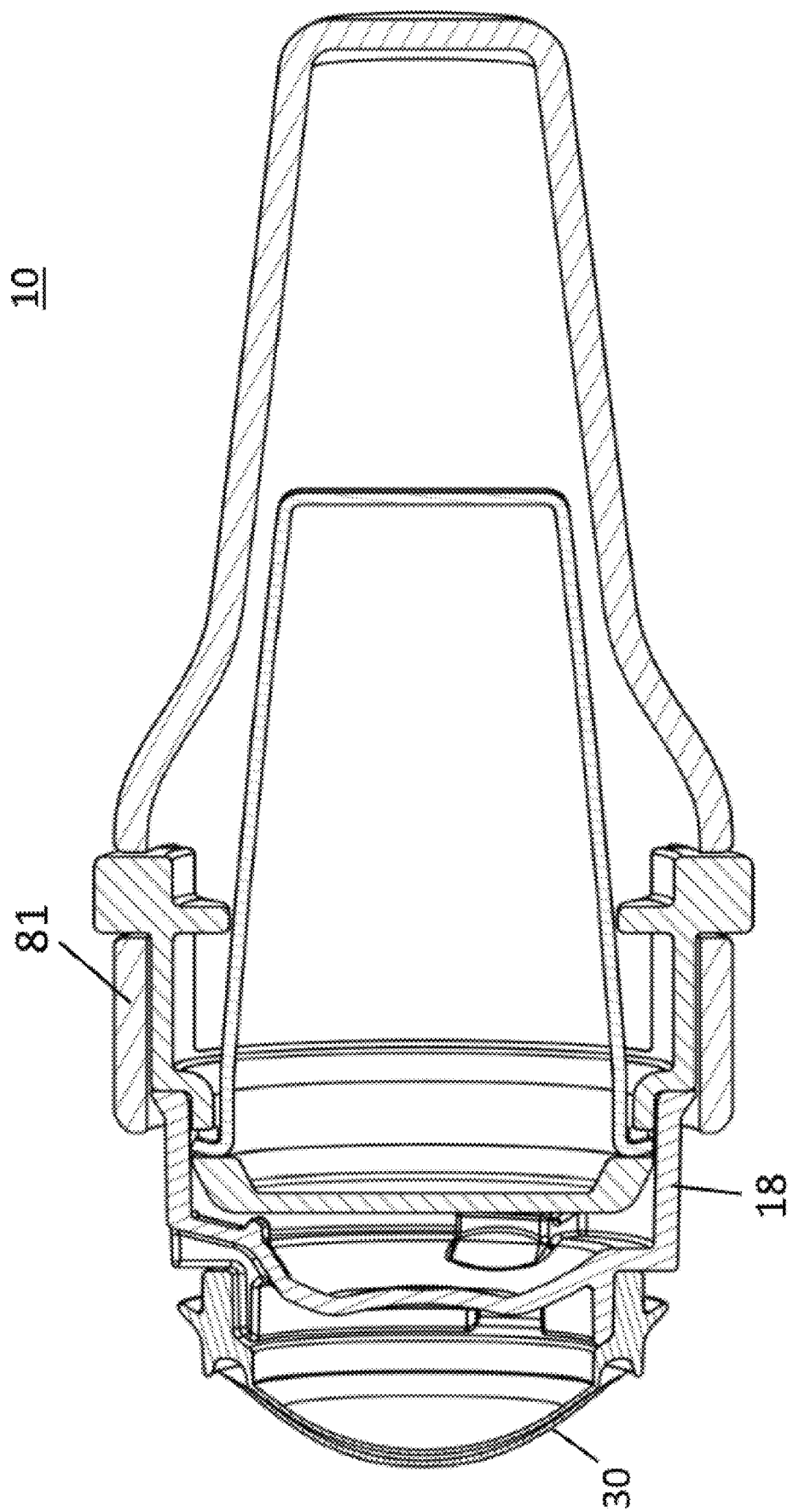
FIG. 32 is a cross-sectional view of the contact lens tool including a gripper, stacking portion, capture portion and lens according to one or more embodiments of the present invention.

FIGS. 30, 31 and 32 depict several embodiments of a gripper 81 for capturing and releasing a stack portion 18.

Particular embodiments and features have been described with reference to the drawings. It is to be understood that these descriptions are not limited to any single embodiment or any particular set of features, and that similar embodiments and features may arise or modifications and additions may be made without departing from the scope of these descriptions and the spirit of the appended claims.

The invention claimed is:

1. A contact lens tool comprising:
a first capture portion defining a first outer edge for capturing a first perimeter of a first contact lens;
a first stack portion engaged or coupled with the first capture portion, and defining a first stack edge positioned distal the first outer edge and defining a first circumference greater than the first outer edge;
an end stack portion defining an end stack edge defining an end circumference greater than the first outer edge and selectively engaged within the first capture portion for creating a fluid-tight seal therebetween.

2. The contact lens tool of claim 1, wherein the first capture portion and the first stack portion are unitarily formed and are essentially comprised of a deformable material.

3. The contact lens tool of claim 1, wherein the first capture portion is essentially comprised of a deformable material and is coupled to the first stack portion essentially comprised of a rigid material.

4. The contact lens tool of claim 1, wherein the first capture portion further defines a first convex lens portion extending between the first outer edge for contouring the first contact lens.

5. The contact lens tool of claim 4, wherein the first capture portion further defines an annular groove between the first outer edge and the first convex lens portion.

6. The contact lens tool of claim 1, further comprising a circumferential first wall portion extending away from the first outer edge and towards the first stack portion, the first wall portion defined by the first capture portion or by the first capture portion and the first stack portion.

7. The contact lens tool of claim 6, wherein the first wall portion defines a first flange externally extending from the first wall portion for creating a seal between the end stack edge and the first capture portion.

8. The contact lens tool of claim 1, further comprising a floor extending between the first stack edge.

9. The contact lens tool of claim 8, wherein the floor and/or wall portion defines one or more clefts for permitting fluid flow therethrough.

10. The contact lens tool of claim 1, further comprising an end floor extending between the end stack edge.

11. The contact lens tool of claim 10, wherein the end floor defines end ridges for engaging the contact lens and securing the contact lens into position.

12. The contact lens tool of claim 1, wherein the capture portion defines at least one lens wing extending internally and away from the first contact lens.

13. The contact lens tool of claim 12, wherein the capture portion defines at least two lens wings and at least one cleft therebetween for permitting fluid flow therethrough.

14. The contact lens tool of claim 1, further comprising a stack handle extending externally of the stack edge.

15. The contact lens tool of claim 1, further comprising a stack container for housing the first capture portion, the first stack portion and the end stack portion.

16. The contact lens tool of claim 15, wherein the stack container defines a plurality of stack arms for selectively engaging the end stack portion.

17. The contact lens tool of claim 1, wherein the end stack edge defines an aperture therethrough.

18. The contact lens tool of claim 17, further comprising a seal configured to wrap around the end stack edge and hermitically seal the aperture.

19. The contact lens tool of claim 1, further comprising:
a second capture portion defining a second outer edge for capturing a second perimeter of a second contact lens;
a second stack portion engaged or coupled with the second capture portion, and defining a second stack edge positioned distal the second outer edge and defining a second circumference greater than the second outer edge;
wherein the first stack edge is selectively engaged within the second capture portion for creating a fluid-tight seal therebetween.

20. The contact lens tool of claim 19, further comprising a stack container for housing the first capture portion, the first stack portion, the end stack portion, the second capture portion and the second stack portion.

* * * * *